(12) United States Patent
Lang et al.

(10) Patent No.: US 6,530,959 B1
(45) Date of Patent: Mar. 11, 2003

(54) DYEING COMPOSITION FOR KERATINOUS FIBRES WITH A DIRECT CATIONIC COLORING AGENT AND A SURFACTANT

(75) Inventors: Gérard Lang, Saint Prix (FR); Jean Cotteret, Veneuil sur Seine (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/529,769

(22) PCT Filed: Jul. 28, 1999

(86) PCT No.: PCT/FR99/01866

§ 371 (c)(1),
(2), (4) Date: May 10, 2000

(87) PCT Pub. No.: WO00/10518

PCT Pub. Date: Mar. 2, 2000

(30) Foreign Application Priority Data

Aug. 19, 1998 (FR) ............................................. 98 10546

(51) Int. Cl.$^7$ ................................................. A61K 7/13
(52) U.S. Cl. ...................... 8/405; 8/406; 8/407; 8/408; 8/412; 8/426; 8/435; 8/437
(58) Field of Search ............................ 8/405, 407, 406, 8/408, 412, 426, 435, 437

(56) References Cited

U.S. PATENT DOCUMENTS

| 3,869,454 A | 3/1975 | Lang et al. ................. 260/244 |
| 3,955,918 A | 5/1976 | Lang ............................ 8/10 |
| 3,985,499 A | 10/1976 | Lang et al. ................... 8/10.1 |
| 4,025,301 A | 5/1977 | Lang ............................ 8/10.1 |
| 4,151,162 A | 4/1979 | Lang et al. ................. 260/158 |
| 4,153,065 A | 5/1979 | Lang ............................ 132/7 |
| 4,823,985 A | 4/1989 | Grollier et al. ................ 222/1 |
| 5,001,004 A | 3/1991 | Fitzgerald et al. .......... 428/263 |
| 5,422,031 A | 6/1995 | Nomura et al. ........ 252/174.17 |
| 5,708,151 A | 1/1998 | Möckli ...................... 534/608 |
| 5,747,014 A | 5/1998 | Cauwet et al. ........... 424/70.11 |
| 5,880,299 A * | 3/1999 | Ponsati et al. .............. 554/109 |
| 5,993,490 A | 11/1999 | Rondeau et al. ............... 8/409 |
| 6,001,135 A | 12/1999 | Rondeau et al. ............... 8/407 |

FOREIGN PATENT DOCUMENTS

| DE | 39 18 135 | 12/1990 |
| DE | 40 21 760 | 1/1992 |
| DE | 42 39 390 | 5/1994 |
| DE | 43 36 803 | 5/1995 |
| DE | 43 37 035 | 5/1995 |
| DE | 44 43 645 | 6/1996 |
| EP | 0 531 943 | 3/1993 |
| EP | 0 714 954 | 6/1996 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 586 913 | 3/1987 |
| WO | WO 94/27573 | 12/1994 |
| WO | WO 95/01772 | 1/1995 |
| WO | WO 95/15144 | 6/1995 |
| WO | WO 99/20234 | 4/1999 |
| WO | WO 99/20235 | 4/1999 |

OTHER PUBLICATIONS

English language Derwent Abstract of DE 39 18 135.
English language Derwent Abstract of DE 40 21 760.
English language Derwent Abstract of DE 42 39 390.
English language Derwent Abstract of DE 43 36 803.
English language Derwent Abstract of DE 43 37 035.
English language Derwent Abstract of DE 44 43 645.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, LLP

(57) ABSTRACT

The invention relates to a composition for dyeing keratinous fibres, in particular human keratinous fibers such as hair, comprising, in an appropriate dyeing medium, at least one cationic direct dye of a given formula, and which is characterized in that it contains, in addition, at least one anionic surfactant chosen from the group consisting of acyl isethionates, acyl taurates, sulphosuccinates, acyl sarcosinates, acyl glutamates, polyoxyalkylenated ether carboxylic acids and their salts, fatty glucamide sulphates, alkyl galactoside uronates, anionic derivatives of alkyl polyglucosides and mixtures thereof.

The invention also relates to the dyeing methods and devices using it.

47 Claims, No Drawings

DYEING COMPOSITION FOR KERATINOUS FIBRES WITH A DIRECT CATIONIC COLORING AGENT AND A SURFACTANT

The invention relates to a composition for dyeing keratinous fibres, in particular human keratinous fibres such as hair, comprising, in an appropriate dyeing medium, at least one cationic direct dye of a given formula, and at least one particular anionic surfactant.

The subject of the invention is also the dyeing methods and devices using the said composition.

In the hair domain, it is possible to distinguish two types of dyeing.

The first is the semipermanent or temporary dyeing, or direct dyeing, which involves dyes capable of bringing the natural colour of the hair a more or less marked colour modification which is resistant, where appropriate, to several shampooings. These dyes are called direct dyes; they can be used with or without oxidizing agent. In the presence of oxidizing agent, the aim is to obtain a lightening dyeing. Lightening dyeing is performed by applying to the hair the fresh mixture of a direct dye and of an oxidizing agent and makes it possible in particular to obtain, by lightening of the melanin of the hair, an advantageous effect such as a uniform colour in the case of grey hair or to make the colour stand out in the case of naturally pigmented hair.

The second is permanent dyeing or oxidation dyeing. The latter is performed with so-called "oxidation" dyes comprising oxidation dye precursors and couplers. The oxidation dye precursors, commonly called "oxidation bases" are compounds which are initially colourless or faintly coloured which develop their dyeing power inside the hair in the presence of oxidizing agents added at the time of use, leading to the formation of coloured and dyeing compounds. The formation of these coloured and dyeing compounds results either from an oxidative condensation of the "oxidation bases" with themselves, or an oxidative condensation of the "oxidation bases" with colour modifying compounds commonly called "couplers" and generally present in the dyeing compositions used in oxidation dyeing.

To vary the shades obtained with the said oxidation dyes, or to increase their shimmer, direct dyes are sometimes added to them.

Among the cationic direct dyes available in the field of dyeing of keratinous fibres, especially human keratinous fibres, compounds are already known whose structure is developed in the text which follows; nevertheless, these dyes lead to colours which exhibit characteristics which are still inadequate from the point of view of the intensity and homogeneity of the colour distributed along the fibre; it is said, in this case, that the colour is too selective, and from the point of view of fastness, in terms of resistance to various attacks to which the hair may be subjected (light, adverse weather conditions, shampooings).

However, after major research studies carried out on this question, the applicant has just now discovered that it is possible to obtain novel compositions for dyeing keratinous fibres which are capable of giving intense and only slightly selective colours which are quite resistant nevertheless to the various attacks to which the hair may be subjected, by combining at least one particular anionic surfactant with at least one cationic direct dye known in the prior art and which have the respective formulae defined hereinafter.

This discovery forms the basis of the present invention.

The first subject of the present invention is therefore a composition for dyeing keratinous fibres and in particular human keratinous fibres such as hair, containing in an appropriate dyeing medium, (i) at least one cationic direct dye whose structure corresponds to the formulae (I) to (IV) defined hereinafter, characterized in that it contains in addition (ii) at least one particular anionic surfactant.

(i) The cationic direct dye which can be used according to the present invention is a compound chosen from those of the following formulae (I), (II), (III), (III'), (IV):

a) the compounds of the following formula (I):

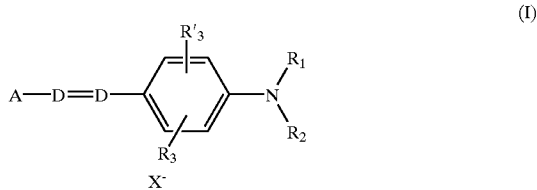

in which:

D represents a nitrogen atom or the —CH group, $R_1$ and $R_2$, which are identical or different, represent a hydrogen atom; a $C_1$–$C_4$ alkyl radical which may be substituted with a —CN, —OH or —NH$_2$ radical or form with a carbon atom of the benzene ring an optionally oxygen-containing or nitrogen-containing heterocycle which may be substituted with one or more $C_1$–$C_4$ alkyl radicals; a 4'-aminophenyl radical, $R_3$ and $R'_3$, which are identical or different, represent a hydrogen or halogen atom chosen from chlorine, bromine, iodine and fluorine, a cyano, $C_1$–$C_4$ alkyl, $C_1$–$C_4$ alkoxy or acetyloxy radical, X$^-$ represents an anion which is preferably chosen from chloride, methylsulphate and acetate, A represents a group chosen from the following structures $A_1$ to $A_{19}$:

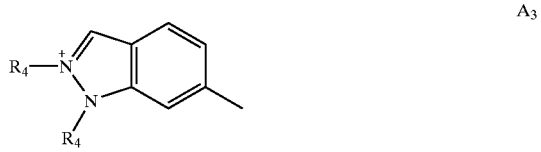

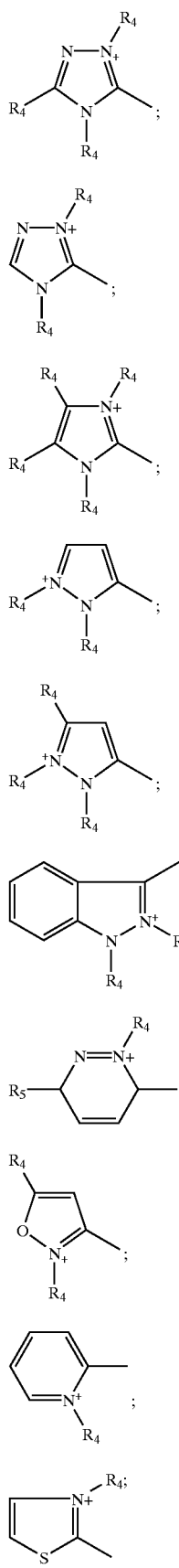
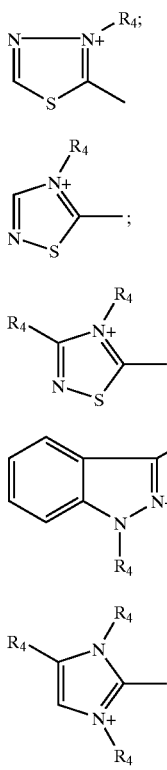
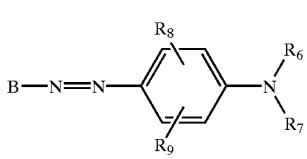

in which $R_4$ represents a $C_1$–$C_4$ alkyl radical which may be substituted with a hydroxyl radical and $R_5$ represents a $C_1$–$C_4$ alkoxy radical, with the proviso that when D represents —CH, A represents $A_4$ or $A_{13}$ and $R_3$ is different from an alkoxy radical, then $R_1$ and $R_2$ do not simultaneously denote a hydrogen atom;

b) the compounds of the following formula (II):

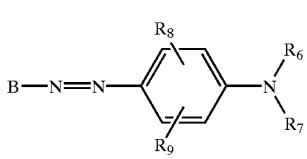

(II)

in which:

$R_6$ represents a hydrogen atom or a $C_1$–$C_4$ alkyl radical, $R_7$ represents a hydrogen atom, an alkyl radical which may be substituted with a —CN radical or with an amino group, a 4'-aminophenyl radical or forms with $R_6$ an optionally oxygen-containing and/or nitrogen-containing heterocycle which may be substituted with a $C_1$–$C_4$ alkyl radical, $R_8$ and $R_9$, which are identical or different, represent a hydrogen atom, a halogen atom such as bromine, chlorine, iodine or fluorine, a $C_1$–$C_4$ alkyl or $C_1$–$C_4$ alkoxy radical, a —CN radical, $X^-$ represents an anion which is preferably chosen from chloride, methylsulphate and acetate, B represents a group chosen from the following structures B1 to B6:

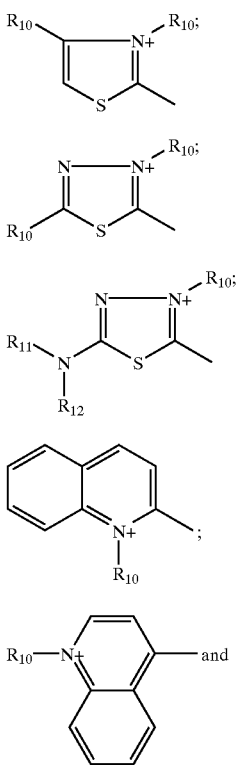

B1

B2

B3

B4

B5

B6 in which $R_{10}$ represents a $C_1$–$C_4$ alkyl radical, $R_{11}$ and $R_{12}$, which are identical or different, represent a hydrogen atom or a $C_1$–$C_4$ alkyl radical;

c) the compounds of the following formulae (III) and (III'):

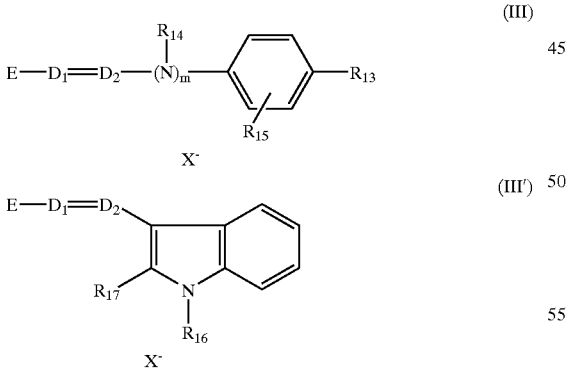

(III)

(III')

in which:
$R_{13}$ represents a hydrogen atom, a $C_1$–$C_4$ alkoxy radical, a halogen atom such as bromine, chlorine, iodine or fluorine or an amino radical,
$R_{14}$ represents a hydrogen atom, a $C_1$–$C_4$ alkyl radical or forms with a carbon atom of the benzene ring a heterocycle which is optionally oxygen-containing and/or substituted with one or more $C_1$–$C_4$ alkyl groups, $R_1$ represents a hydrogen or halogen atom such as bromine, chlorine, iodine of fluorine,
$R_{16}$ and $R_{17}$, which are identical or different, represent a hydrogen atom or a $C_1$–$C_4$ alkyl radical,
$D_1$ and $D_2$, which are identical or different, represent a nitrogen atom or the —CH group,
m=0 or 1, it being understood that when $R_{13}$ represents an unsubstituted amino group, then $D_1$ and $D_2$ simultaneously represent a —CH group and m=0,
$X^-$ represents an anion which is preferably chosen from chloride, methylsulphate and acetate,
E represents a group chosen from the following structures E1 to E8:

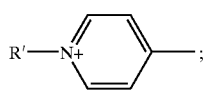

E1

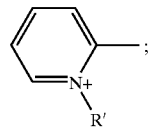

E2

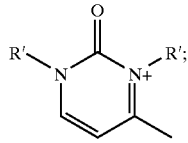

E3

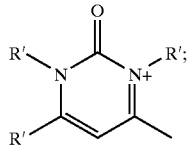

E4

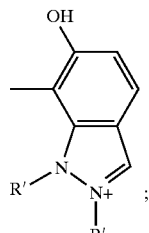

E5

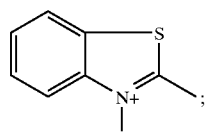

E6

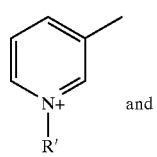

E7

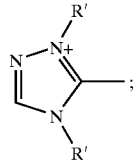

E8 in which R' represents a $C_1$–$C_4$ alkyl radical;

when m=0 and $D_1$ represents a nitrogen atom, then E may also denote a group having the following structure E9:

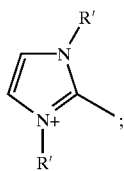

E9 in which R' represents a $C_1$–$C_4$ alkyl radical,
d) the compounds of the following formula (IV):

G—N═N—J       (IV)

in which:
the symbol G represents a group chosen from the following structures $G_1$ to $G_3$:

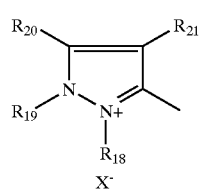

$G_1$

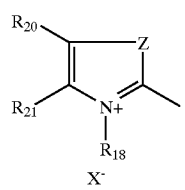

$G_2$

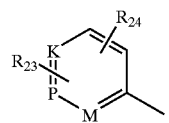

$G_3$ in which structures $G_1$ to $G_3$,
$R_{18}$ denotes a $C_1$–$C_4$ alkyl radical, a phenyl radical which may be substituted with a $C_1$–$C_4$ alkyl radical or a halogen atom chosen from chlorine, bromine, iodine and fluorine;
$R_{19}$ denotes a $C_1$–$C_4$ alkyl radical or a phenyl radical;
$R_{20}$ and $R_{21}$, which are identical or different, represent a $C_1$–$C_4$ alkyl radical, a phenyl radical, or form together in $G_1$ a benzene ring which is substituted with one or more $C_1$–$C_4$ alkyl, $C_1$–$C_4$ alkoxy or $NO_2$ radicals, or form together in $G_2$ a benzene ring which is optionally substituted with one or more $C_1$–$C_4$ alkyl, $C_1$–$C_4$ alkoxy or $NO_2$ radicals;
$R_{20}$ may denote, in addition, a hydrogen atom;
Z denotes an oxygen or sulphur atom or an —$NR_{19}$ group;
M represents a group —CH, —CR (R denoting $C_1$–$C_4$ alkyl), or —$NR_{22}(X^-)_r$;
K represents a group —CH, —CR (R denoting $C_1$–$C_4$ alkyl), or —$NR_{22}(X^-)_r$;
P represents a group —CH, —CR (R denoting $C_1$–$C_4$ alkyl), or —$NR_{22}(X^-)_r$; r denotes zero or 1;
$R_{22}$ represents an $O^-$ atom, a $C_1$–$C_4$ alkoxy radical or a $C_1$–$C_4$ alkyl radical;

$R_{23}$ and $R_{24}$, which are identical or different, represent a hydrogen or halogen atom chosen from chlorine, bromine, iodine and fluorine, a $C_1$–$C_4$ alkyl radical, a $C_1$–$C_4$ alkoxy radical or an —$NO_2$ radical;
$X^-$ represents an anion which is preferably chosen from chloride, iodide, methylsulphate, ethylsulphate, acetate and perchlorate;
with the proviso that
if $R_{22}$ denotes $O^-$, then r denotes zero;
if K or P or M denote —N—($C_1$–$C_4$ alkyl)$X^-$, then $R_{23}$ or $R_{24}$ is different from a hydrogen atom;
if K denotes —$NR_{22}(X^-)_r$, then M=P=—CH, —CR;
if M denotes —$NR_{22}(X^-)_r$, then K=P=—CH, —CR;
if P denotes —$NR_{22}(X^-)_r$, then K=M and denote —CH or —CR;
if Z denotes a sulphur atom with $R_{21}$ denoting $C_1$–$C_4$ alkyl, then $R_{20}$ is different from a hydrogen atom;
if Z denotes —$NR_{22}$ with $R_{19}$ denoting $C_1$–$C_4$ alkyl, then at least one of the $R_{18}$, $R_{20}$ or $R_{21}$, radicals of the group having the structure $G_2$ is different from a $C_1$–$C_4$ alkyl radical;
the symbol J represents:
(a) a group having the following structure $J_1$:

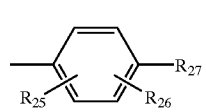

$J_1$ in which structure $J_1$,
$R_{25}$ represents a hydrogen atom, a halogen atom chosen from chlorine, bromine, iodine and fluorine, a $C_1$–$C_4$ alkyl radical, a $C_1$–$C_4$ alkoxy radical, a radical —OH, —$NO_2$, —$NHR_{28}$, —$NR_{29}R_{30}$, —NHCO($C_1$–$C_4$alkyl), or forms with $R_{26}$ a 5- or 6-membered ring containing or otherwise one or more heteroatoms chosen from nitrogen, oxygen or sulphur;
$R_{26}$ represents a hydrogen atom, a halogen atom chosen from chlorine, bromine, iodine and fluorine, a $C_1$–$C_4$ alkyl or $C_1$–$C_4$ alkoxy radical, or forms with $R_{27}$ or $R_{28}$ a 5- or 6-membered ring containing or otherwise one or more heteroatoms chosen from nitrogen, oxygen or sulphur;
$R_{27}$ represents a hydrogen atom, an —OH radical, an —$NHR_{28}$ radical, an —$NR_{29}R_{30}$ radical;
R28 represents a hydrogen atom, a $C_1$–$C_4$ alkyl radical, a $C_1$–$C_4$ monohydroxyalkyl radical, a $C_2$–$C_4$ polyhydroxyalkyl radical, a phenyl radical;
$R_{29}$ and $R_{30}$, which are identical or different, represent a $C_1$–$C_4$ alkyl radical, a $C_1$–$C_4$ monohydroxyalkyl radical, a $C_2$–$C_4$ polyhydroxyalkyl radical;
(b) a 5- or 6- membered nitrogen-containing heterocycle group which is capable of containing other heteroatoms and/or carbonyl-containing groups and which may be substituted with one or more $C_1$–$C_4$ alkyl, amino or phenyl radicals, and in particular a group having the following structure J₂:

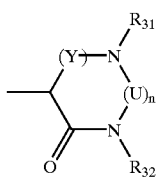

in which structure J₂,

R₃₁ and R₃₂, which are identical or different, represent a hydrogen atom, a $C_1$–$C_4$ alkyl radical, a phenyl radical;

Y denotes the —CO— radical or the radical

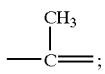

n=0 or 1, with, when n denotes 1, U denotes the —CO— radical.

In the structures (I) to (IV) defined above, the $C_1$–$C_4$ alkyl or alkoxy group preferably denotes methyl, ethyl, butyl, methoxy or ethoxy.

The cationic direct dyes of formulae (I), (II), (III) and (III') which can be used in the dyeing compositions in accordance with the invention are known compounds which are described, for example, in patent applications WO 95/01772, WO 95/15144 and EP-A-0,714,954. Those of formula (IV) which can be used in the dyeing compositions in accordance with the invention are known compounds which are described, for example, in patent applications FR-2,189,006, FR-2,285,851 and FR-2,140,205 and its certificates of addition.

Among the cationic direct dyes of formula (I) which can be used in the dyeing compositions in accordance with the invention, there may be mentioned more particularly the compounds corresponding to the following structures (I1) to (I54):

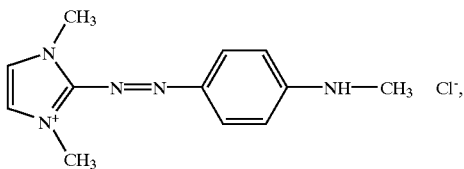
(I1)

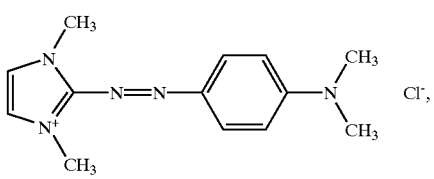
(I2)

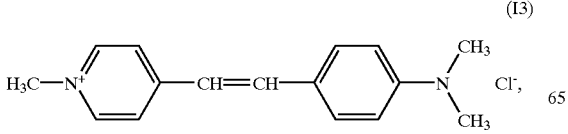
(I3)

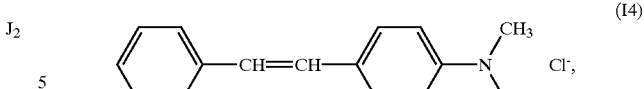
(I4)

(I5)

(I6)

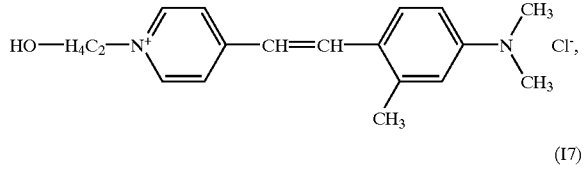
(I7)

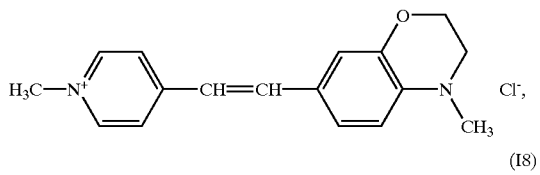
(I8)

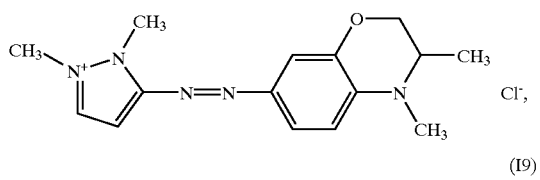
(I9)

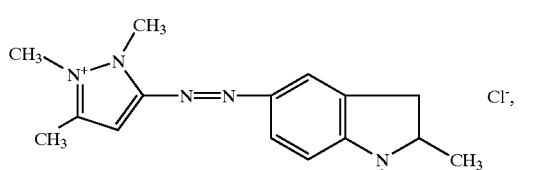
(I10)

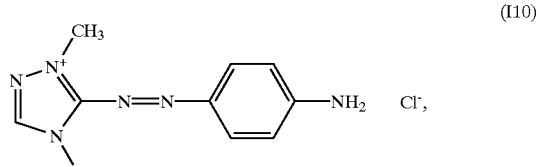
(I11)

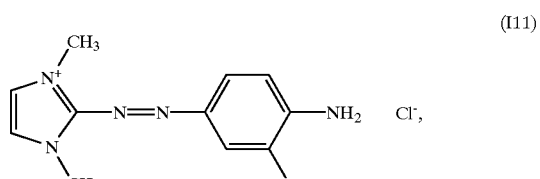
(I12)

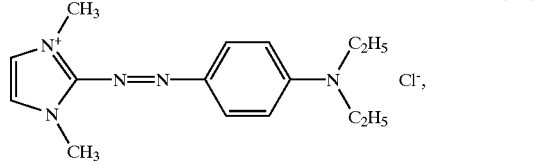

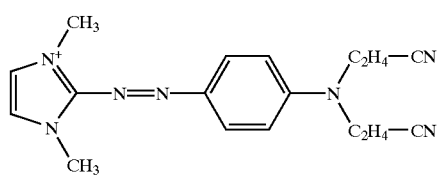 (I13)
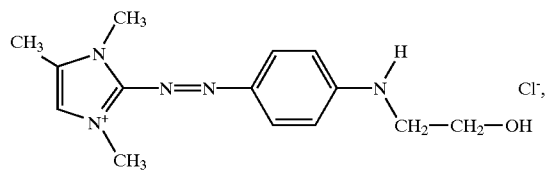 (I21)
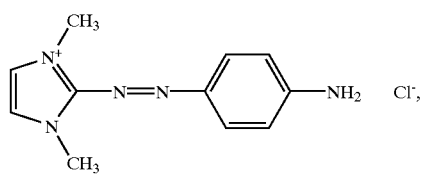 (I14)
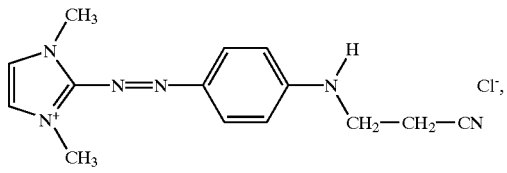 (I22)
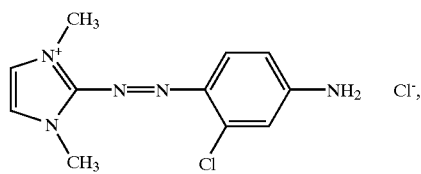 (I15)
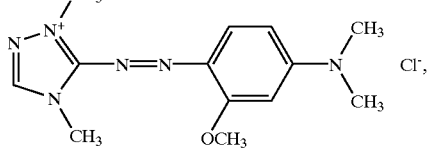 (I23)
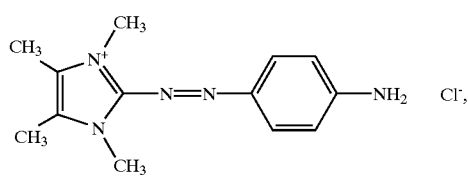 (I16)
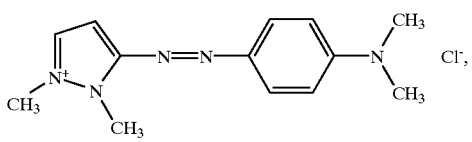 (I24)
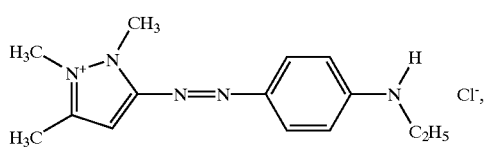 (I17)
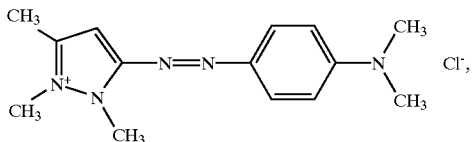 (I25)
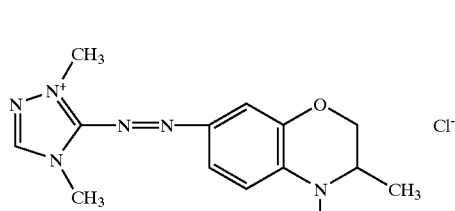 (I18)
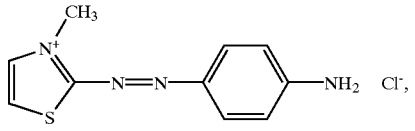 (I26)
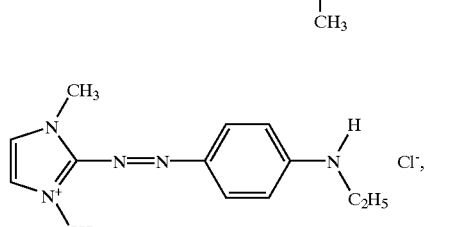 (I19)
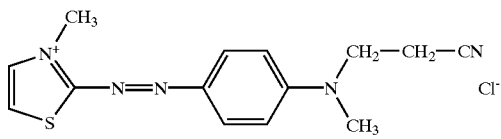 (I27)
 (I20)
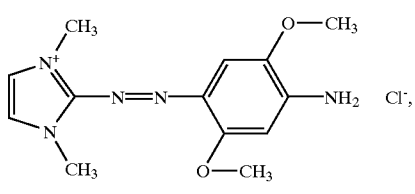 (I28)
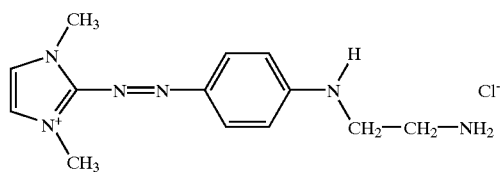
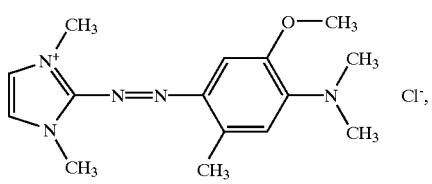 (I29)

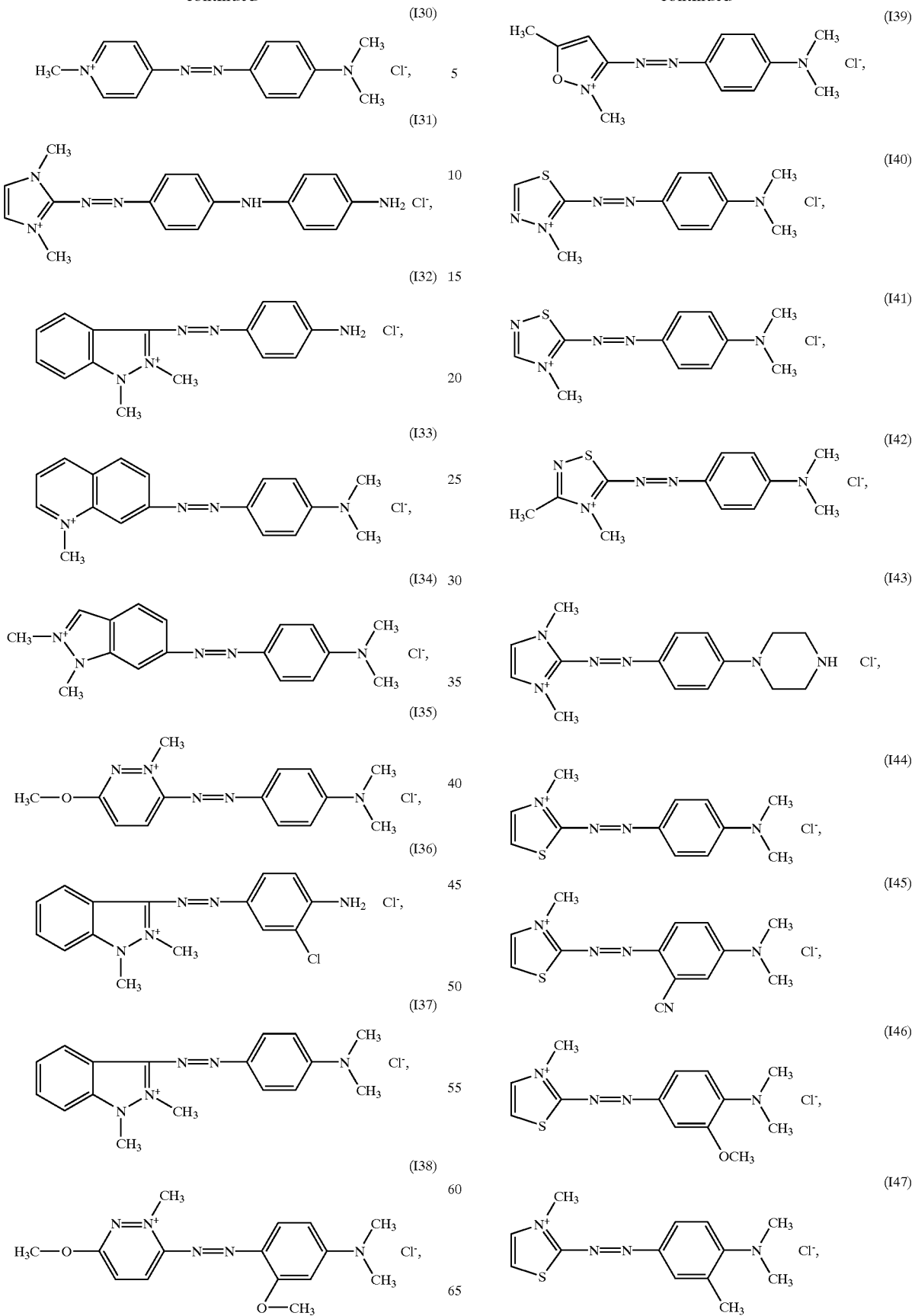

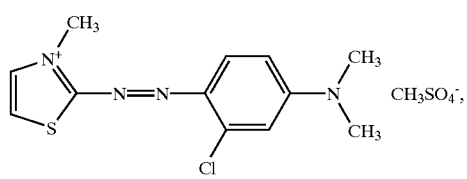 (I48)

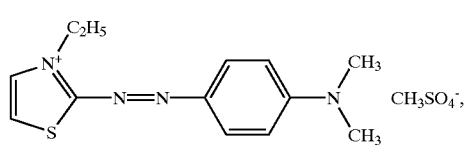 (I49)

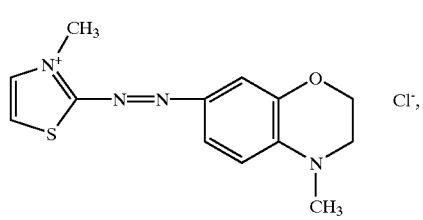 (I50)

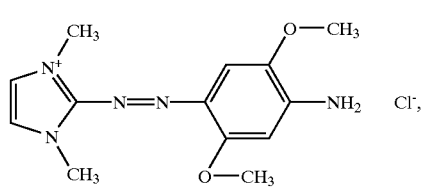 (I51)

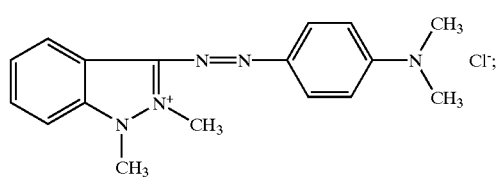 (I52)

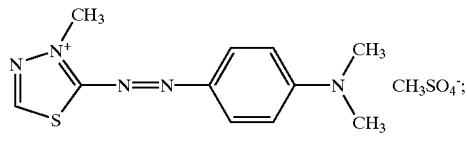 (I53)

and

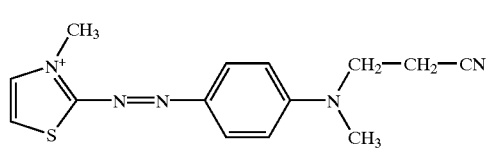 (I54)

Among the compounds having the structures (I1) to (I54) which are described above, the compounds corresponding to the structures (I1), (I2), (I14) and (I31) are most particularly preferred.

Among the cationic direct dyes of formula (II) which can be used in the dyeing compositions in accordance with the invention, there may be mentioned more particularly the compounds corresponding to the following structures (II1) to (II9):

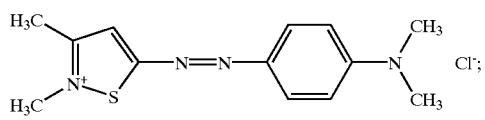 (II1)

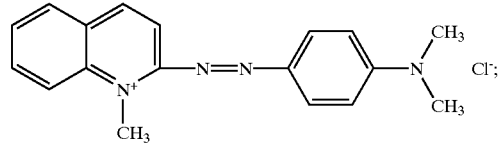 (II2)

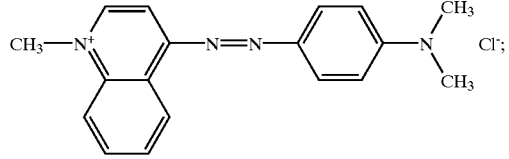 (II3)

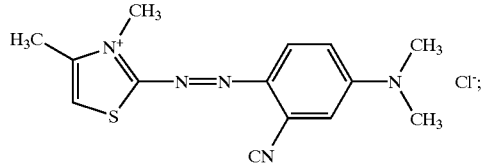 (II4)

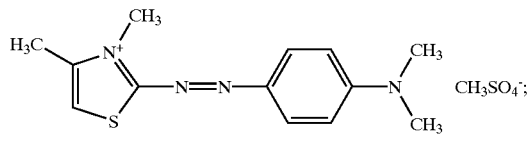 (II5)

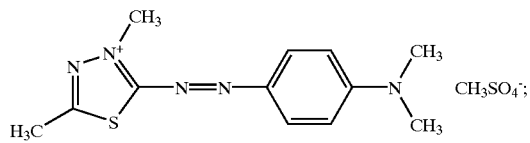 (II6)

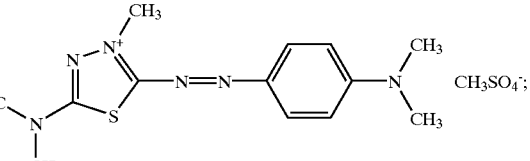 (II7)

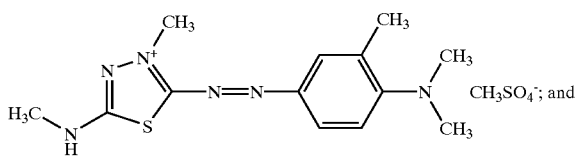 (II8)

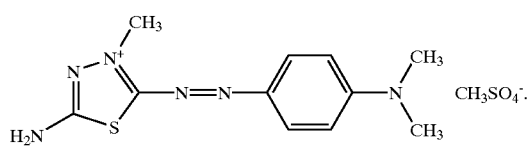 (II9)

Among the cationic direct dyes of formula (III) which can be used in the dyeing compositions in accordance with the invention, there may be mentioned more particularly the compounds corresponding to the following structures (III1) to (III18):

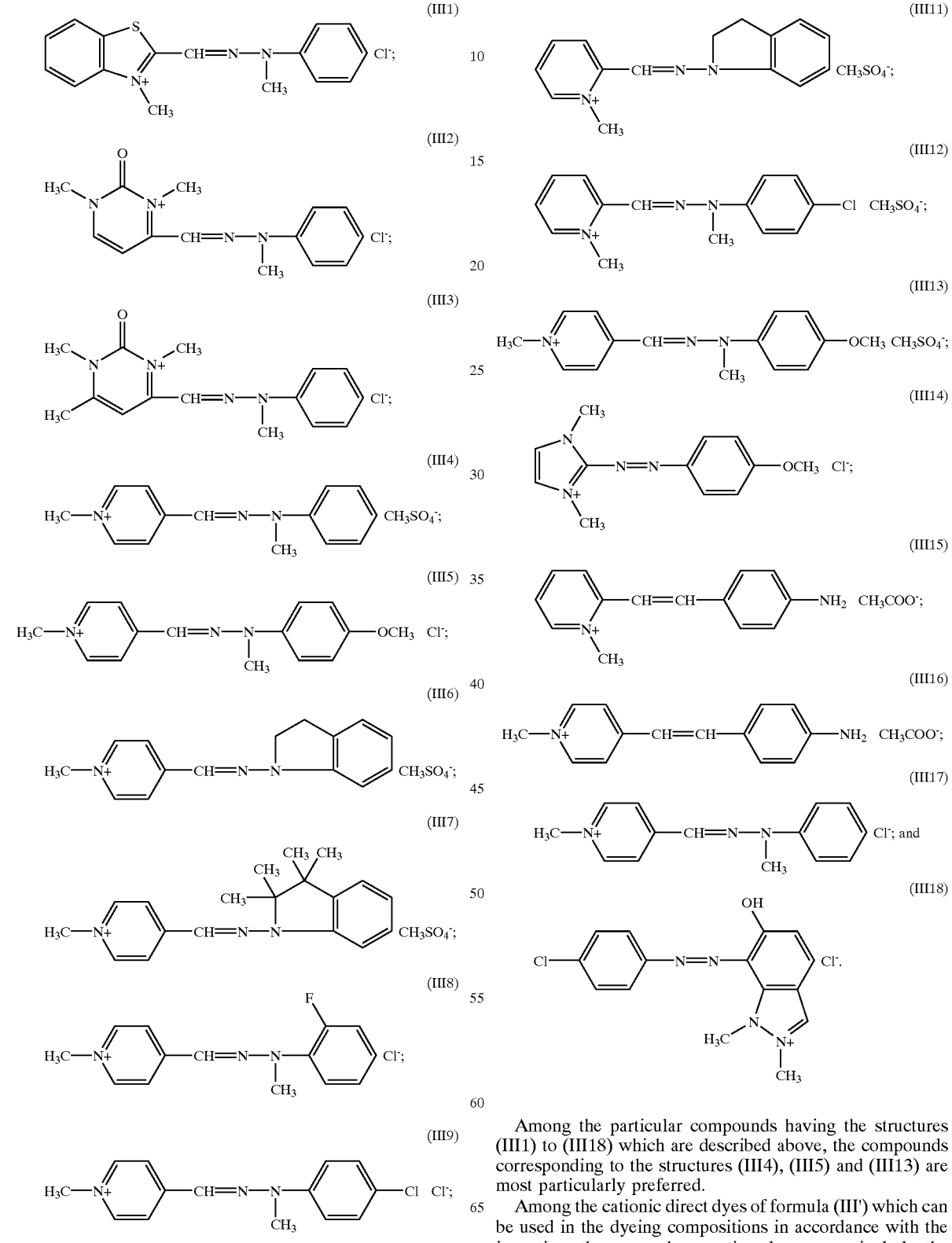

Among the particular compounds having the structures (III1) to (III18) which are described above, the compounds corresponding to the structures (III4), (III5) and (III13) are most particularly preferred.

Among the cationic direct dyes of formula (III') which can be used in the dyeing compositions in accordance with the invention, there may be mentioned more particularly the compounds corresponding to the following structures (III'1) to (III'3):

(III'1) [structure]

(III'2) [structure]

(III'3) [structure]

Among the cationic direct dyes of formula (IV) which can be used in the dyeing compositions in accordance with the invention, there may be mentioned more particularly the compounds having the following structures $(IV)_1$ to $(IV)_{77}$:

-continued (IV)₁₄, (IV)₁₅, (IV)₁₆, (IV)₁₇, (IV)₁₈, (IV)₁₉, (IV)₂₀, (IV)₂₁, (IV)₂₂, (IV)₂₃, (IV)₂₄, (IV)₂₅, (IV)₂₆, (IV)₂₇, (IV)₂₈, (IV)₂₉

-continued
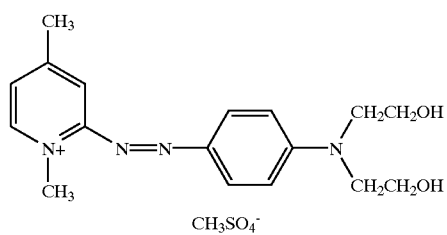
(IV)30
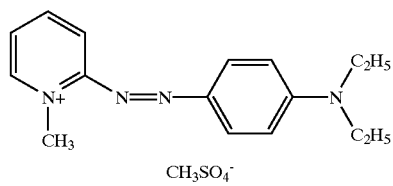
(IV)31
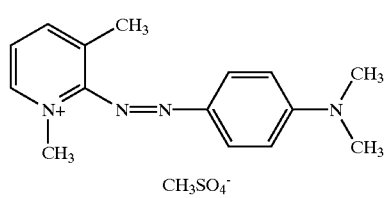
(IV)32
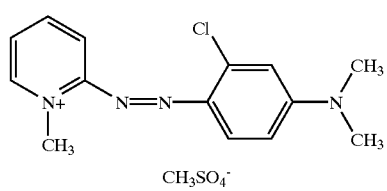
(IV)33
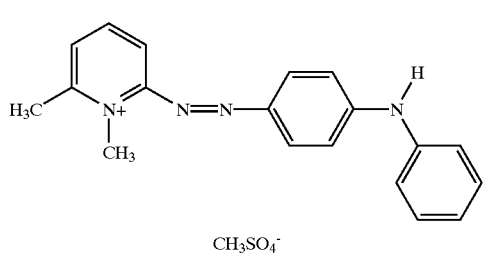
(IV)34
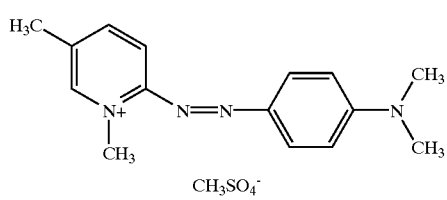
(IV)35
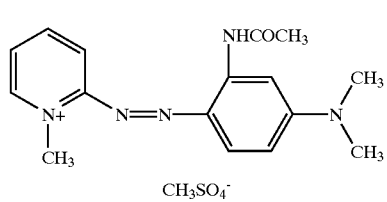
(IV)36
-continued
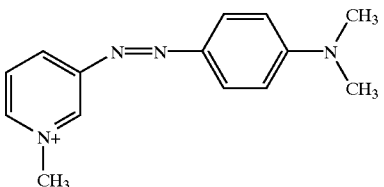
(IV)37
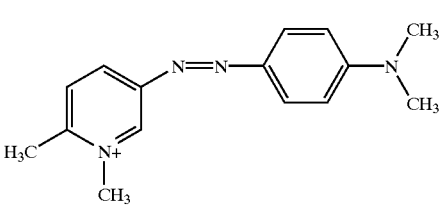
(IV)38
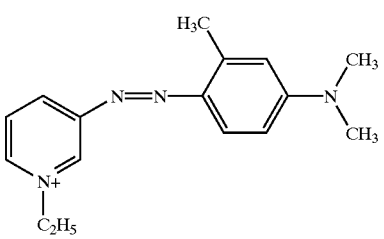
(IV)39
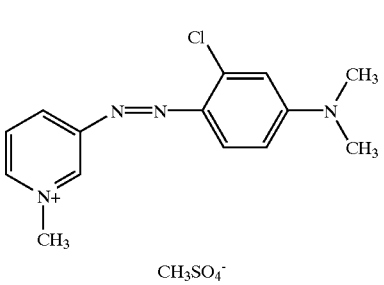
(IV)40
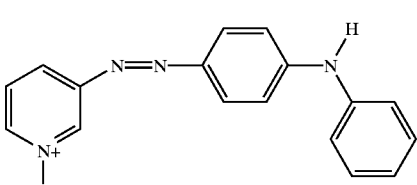
(IV)41
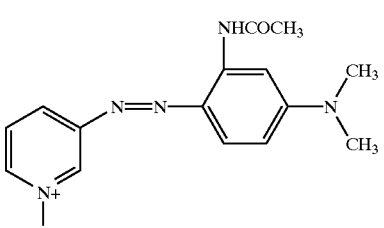
(IV)42

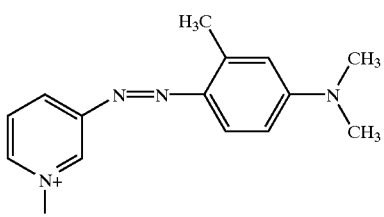
(IV)₄₃
Br⁻
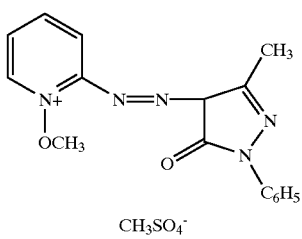
(IV)₄₄
CH₃SO₄⁻
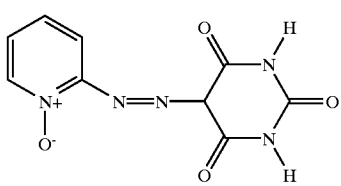
(IV)₄₅
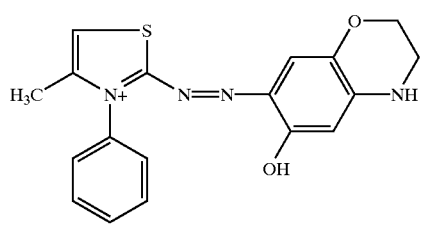
(IV)₄₆
ClO₄⁻
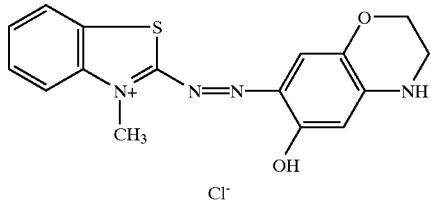
(IV)₄₇
ClO₄⁻
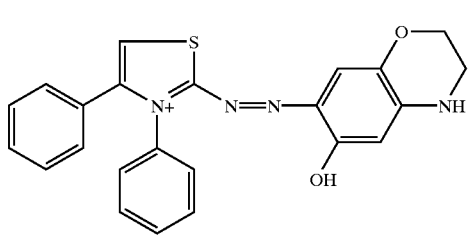
(IV)₄₈
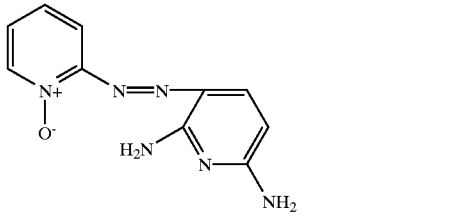
(IV)₄₉
I⁻
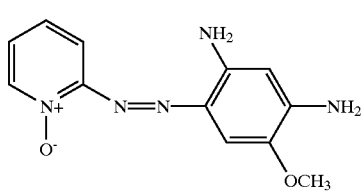
(IV)₅₀
ClO₄⁻
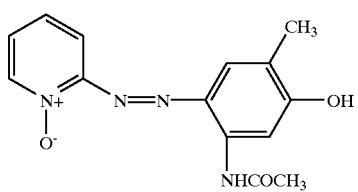
(IV)₅₁
Cl⁻
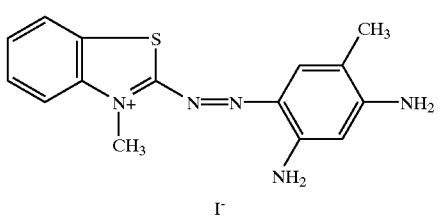
(IV)₅₂
ClO₄⁻
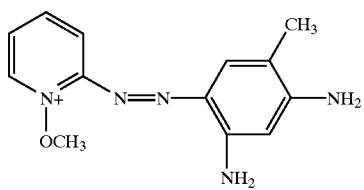
(IV)₅₃
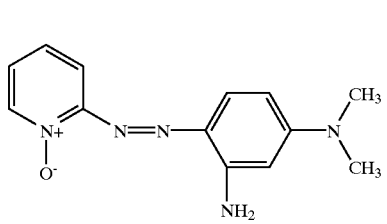
(IV)₅₄
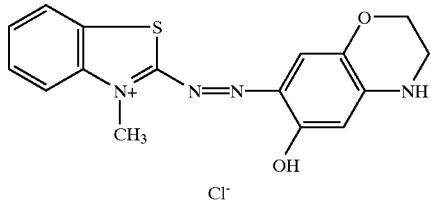
(IV)₅₅
ClO₄⁻
(IV)₅₆

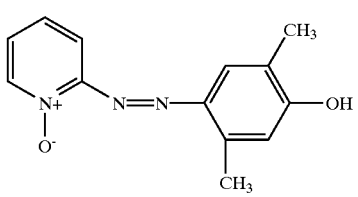 (IV)₅₇
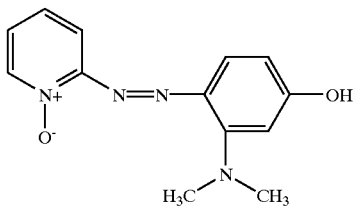 (IV)₅₈
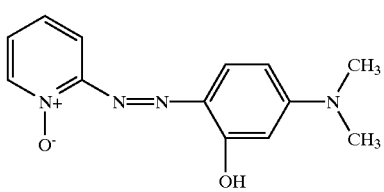 (IV)₅₉
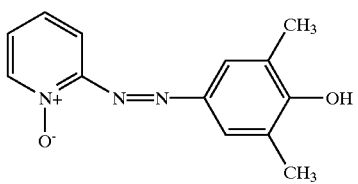 (IV)₆₀
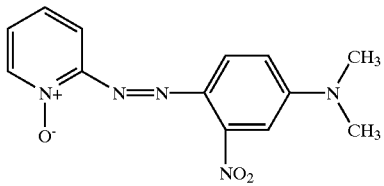 (IV)₆₁
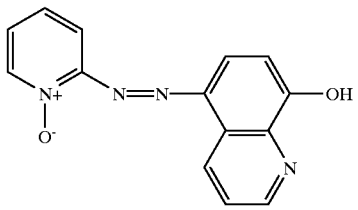 (IV)₆₂
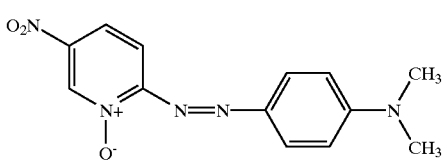 (IV)₆₃
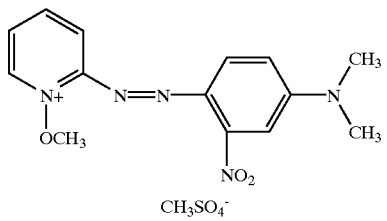 (IV)₆₄
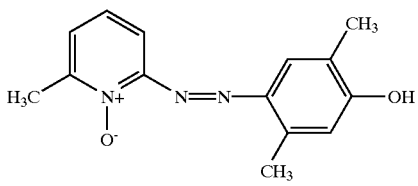 (IV)₆₅
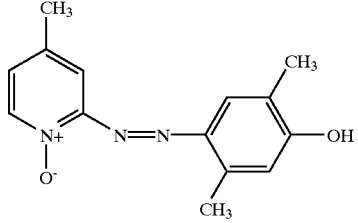 (IV)₆₆
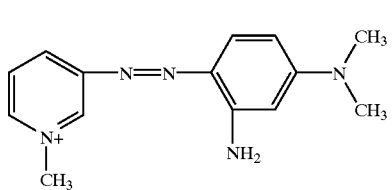 (IV)₆₇
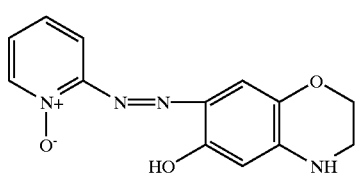 (IV)₆₈
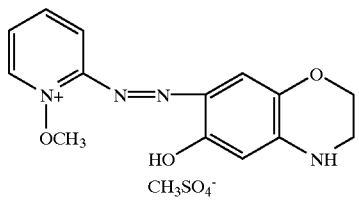 (IV)₆₉
(IV)₇₀

-continued

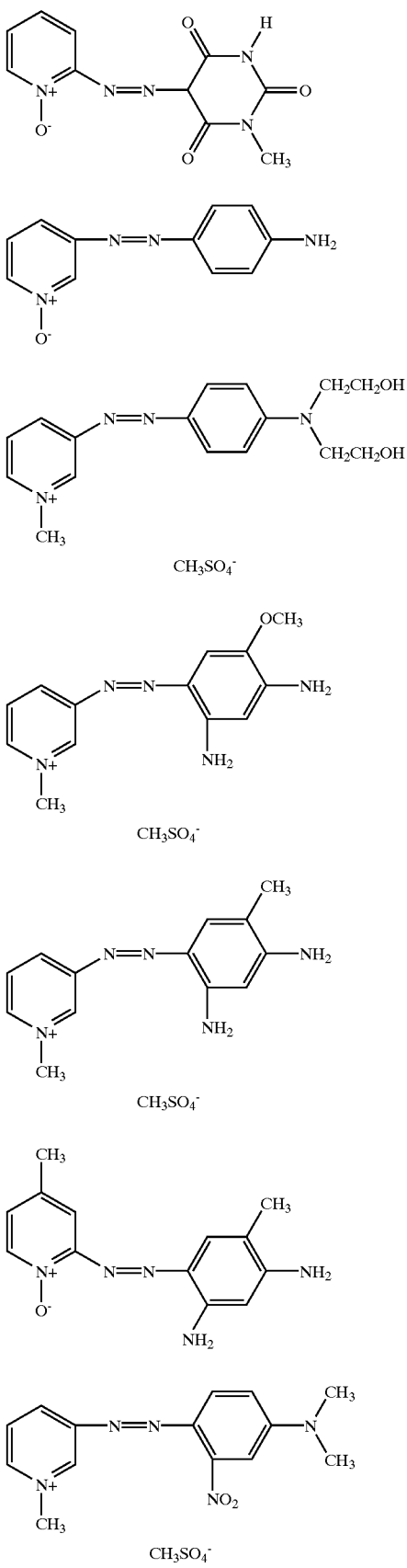

The cationic direct dye(s) used according to the invention preferably represent from 0.001 to 10% by weight approximately of the total weight of the dyeing composition and still more preferably from 0.005 to 5% by weight approximately of this weight.

(ii) The anionic surfactant which can be used according to the present invention is chosen from the group consisting of:
- (ii)$_1$—acyl isethionates;
- (ii)$_2$—acyl taurates;
- (ii)$_3$—sulphosuccinates;
- (ii)$_4$—acyl sarcosinates;
- (ii)$_5$—acyl glutamates;
- (ii)$_6$—polyoxyethylenated ether carboxylic acids and their salts;
- (ii)$_7$—fatty glucamide sulphates;
- (ii)$_8$—alkyl galactoside uronates;
- (ii)$_9$—anionic derivatives of alkyl polyglucosides;
- (ii)$_{10}$—mixtures thereof.

The preferred acyl isethionates (ii)$_1$ and acyl taurates (ii)$_2$ in accordance with the invention correspond to the following general structure:

$$R^1-CH_2-CH_2-SO_3^-M^+ \quad (V)$$

where $R^1$ denotes an $R^2COO$ group or an $R^2CONR^3$ group with $R^2$ denoting a saturated or unsaturated, linear or branched $C_8$–$C_{30}$ aliphatic group and $R^3$ denoting a hydrogen atom or a $C_1$–$C_4$ alkyl radical, and where M denotes H, ammonium, Na or K or an organic amine, in particular alkanolamine, residue.

The preferred sulphosuccinates (ii)$_3$ which can be used according to the invention correspond to the following general structure:

$$R^2O-CO-\underset{\underset{SO_3^-}{|}}{CH}-CH_2-COO^- \quad 2M^+ \quad (VI)$$

where $R^2$ and M have the same meanings indicated above for formula (V).

The preferred acyl sarcosinates (ii)$_4$ and acyl glutamates (ii)$_5$ which can be used according to the invention correspond to the following general structure:

$$R^2-CO-\underset{\underset{R^4}{|}}{N}-CH\underset{R^5}{\overset{COO^- \; M^+}{\diagup}} \quad (VII)$$

where $R^2$ and M have the same meanings indicated above for formula (V);

$R^4$ denotes $CH_3$ and $R^5$ denotes hydrogen-, or alternatively, $R^4$ denotes hydrogen and $R^5$ denotes $-CH_2CH_2COO^-$ $M^+$.

The polyoxyalkylenated ether carboxylic acids and their salts (ii)$_6$ in accordance with the invention are preferably those comprising from 2 to 50 ethylene oxide groups, and mixtures thereof. The anionic surfactants of the polyoxyalkylenated ether carboxylic acid or salt type are in particular those which correspond to the following formula (VIII):

$$R^5-(OC_2H_4)_n-OCH_2COOA \quad (VIII)$$

in which:

$R^6$ denotes an alkyl or alkylaryl group, and n is an integer or a decimal number (mean value) which may vary from 2 to 24 and preferably from 3 to 10, the alkyl radical having between 6 and 20 carbon atoms approximately, and aryl preferably denoting phenyl, A denotes H, ammonium, Na, K, Li, Mg or a monoethanolamine or triethanolamine residue. It is also possible to use mixtures of compounds of formula (VIII), in particular mixtures in which the R6 groups are different.

Compounds of formula (VIII) are sold for example by the company KAO under the names AKYPOS (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, RO 50) or by the company SANDOZ under the names SANDOPAN (DTC Acid, DTC).

The fatty glucamide sulphates (ii)$_7$ which can be used according to the invention are those described in patent application DE-4443645, the content of which forms an integral part of the description.

The alkyl galactoside uronates (ii)$_8$ which can be used according to the invention are those described in patent EP-B-0,701,430, the content of which forms an integral part of the description.

The anionic derivatives of alkyl polyglucoside (ii)$_9$ are preferably chosen from:

alkyl polyglucoside sulphates or sulphonates or mixtures thereof;

alkyl polyglucoside ether carboxylates;

alkyl polyglucoside sulphosuccinates;

alkyl polyglucoside isethionates;

alkyl polyglucoside phosphates.

These anionic derivatives of alkyl polyglucoside are in particular described in applications DE-3918135, DE-4021760, DE-4239390, DE-4336803, DE-4337035 and patent U.S. Pat. No. 5,001,004.

The anionic surfactants (ii) used according to the invention preferably represent from 0.05 to 30% by weight approximately of the total weight of the dyeing composition and still more preferably from 0.1 to 15% by weight approximately of this weight.

The appropriate dyeing medium (or carrier) generally consists of water or of a mixture of water and of at least one organic solvent for solubilizing the compounds which would not be sufficiently soluble in water. As organic solvent, there may be mentioned for example the $C_1$–$C_4$ lower alkanols such as ethanol and isopropanol, the aromatic alcohols such as benzyl alcohol as well as similar products and mixtures thereof.

The solvents may be present in proportions preferably of between 1 and 40% by weight approximately relative to the total weight of the dyeing composition, and still more preferably between 5 and 30% by weight approximately.

The pH of the dyeing composition in accordance with the invention is generally between 2 and 11 approximately, and preferably between 5 and 10 approximately. It may be adjusted to the desired value by means of acidifying or alkalinizing agents normally used in dyeing keratinous fibres.

Among the acidifying agents, there may be mentioned, by way of example, the inorganic or organic acids such as hydrochloric acid, orthophosphoric acid, sulphuric acid, carboxylic acids such as acetic acid, tartaric acid, citric acid, lactic acid, sulphonic acids.

Among the alkalinizing agents, there may be mentioned, by way of example, aqueous ammonia, alkali metal carbonates, alkanolamines such as mono-, di- and triethanolamines as well as derivatives thereof, sodium or potassium hydroxides and the compounds having the following formula (VIII):

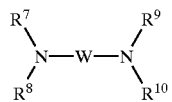

(IX)

in which W is a propylene residue which is optionally substituted with a hydroxyl group or a $C_1$–$C_6$ alkyl radical; $R^7$, $R^8$, $R^9$ and $R^{10}$, which are identical or different, represent a hydrogen atom, a $C_1$–$C_6$ alkyl radical or a $C_1$–$C_6$ hydroxyalkyl radical.

The dyeing composition in accordance with the invention may, in addition to the cationic direct dye(s) (i) defined above, contain one or more additional direct dyes which may for example be chosen from the nitrobenzene dyes, theanthraquinone dyes, the naphthoquinone dyes, the triarylmethane dyes, the xanthene dyes, the noncationic azo dyes.

When it is intended for oxidation dyeing, the dyeing composition in accordance with the invention contains, in addition to the cationic direct dye(s) (i), one or more oxidation bases chosen from the oxidation bases conventionally used for oxidation dyeing and among which there may be mentioned in particular the para-phenylenediamines, the bis-phenylalkylenediamines, the para-aminophenols, the ortho-aminophenols and the heterocyclic bases. When they are used, the oxidation base(s) preferably represent from 0.0005 to 12% by weight approximately of the total weight of the dyeing composition, and still more preferably from 0.005 to 6% by weight approximately of this weight.

When it is intended for oxidation dyeing, the dyeing composition in accordance with the invention may also contain, in addition to the cationic direct dye (i) and the anionic surfactant (ii) as well as oxidation bases, one or more couplers so as to modify or increase the shimmer of the shades obtained using the cationic direct dye(s) (i) and the oxidation base(s).

The couplers which can be used in the dyeing composition in accordance with the invention may be chosen from the couplers conventionally used in oxidation dyeing and among which there may be mentioned in particular the meta-phenylenediamines, the meta-aminophenols, the meta-diphenols and the heterocyclic couplers.

When they are present, the coupler(s) preferably represent from 0.0001 to 10%. by weight approximately of the total weight of the dyeing composition and still more preferably from 0.005 to 5% by weight approximately of this weight.

The dyeing composition in accordance with the invention may also contain various adjuvants which are conventionally used in hair-dyeing compositions, such as antioxidants, penetrating agents, sequestrants, perfumes, buffers, dispersing agents, film-forming agents, ceramides, preservatives, screening agents and opacifying agents.

Of course, persons skilled in the art will be careful to choose this or these optional additional compounds such that the advantageous properties intrinsically attached to the dyeing composition in accordance with the invention are not, or not substantially, altered by the addition(s) envisaged.

The dyeing composition according to the invention may be provided in various forms, such as in the form of liquids, shampoos, creams, gels, or in any other form appropriate for dyeing keratinous fibres, and in particular human hair. It may be obtained by freshly mixing a composition, which is optionally pulverulent, containing the cationic direct dye(s) with a composition containing the anionic surfactant.

When the combination of the cationic direct dye (i) and of the anionic surfactant (ii) according to the invention is used in a composition intended for oxidation dyeing (one or more oxidation bases are then used, optionally in the presence of one or more couplers) or when it is used in a composition intended for direct lightening dyeing, then the dyeing composition in accordance with the invention contains, in addition, at least one oxidizing agent chosen for example from hydrogen peroxide, urea peroxide, alkali metal bromates, persalts such the perborates and persulphates, and enzymes such as peroxidases, laccases and oxidoreductases containing two electrons. The use of hydrogen peroxide or of enzymes is particularly preferred.

Another subject of the invention is a method of dyeing keratinous fibres and in particular human keratinous fibres such as hair using the dyeing composition as defined above.

According to a first variant of this dyeing method in accordance with the invention, at least one dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more preferably 5 and 40 minutes.

According to a second variant of this dyeing method in accordance with the invention, at least one dyeing composition as defined above is applied to the fibres for a sufficient time to develop the desired colour, with no final rinsing.

According to a particular embodiment of this dyeing method, and when the dyeing composition in accordance with the invention contains at least one oxidation base and at least one oxidizing agent, the dyeing method comprises a preliminary stage consisting of storing in a separate form, on the one hand, a composition (A1) comprising, in an appropriate dyeing medium, at least one cationic direct dye (i) as defined above and at least one oxidation base and, on the other hand, a composition (B1) containing, in an appropriate dyeing medium, at least one oxidizing agent, and then mixing them at the time of use before applying this mixture to the keratinous fibres, the composition (A1) or the composition (B1) containing the anionic surfactant (ii) as defined above.

According to another particular embodiment of this dyeing method, and when the dyeing composition in accordance with the invention contains at least one oxidizing agent, the dyeing method comprises a preliminary stage consisting of storing in a separate form, on the one hand, a composition (A2) comprising, in an appropriate dyeing medium, at least one cationic direct dye (i) as defined above and, on the other hand, a composition (B2) containing, in an appropriate dyeing medium, at least one oxidizing agent, and then mixing them at the time of use before applying this mixture to the keratinous fibres, the composition (A2) or the composition (B2) containing the anionic surfactant as defined above.

Another subject of the invention is a multicompartment device or dyeing "kit" or any other multicompartment packaging system in which a first compartment contains composition (A1) or (A2) as defined above and a second compartment contains composition (B1) or (B2) as defined above. These devices may be equipped with a means allowing the desired mixture to be delivered to the hair, such as the devices described in patent FR-2,586,913 in the applicant's name.

The following examples are intended to illustrate the invention without, however, limiting the scope thereof.

EXAMPLES

Examples 1 to 5

The five direct dyeing compositions which are assembled in the following table were prepared: (all contents expressed in grams)

|  | Example 1 | Example 2 | Example 3 | Example 4 | Example 5 |
|---|---|---|---|---|---|
| Cationic direct dye of formula (I1) | 0.2 | | | | |
| Cationic direct dye of formula (I14) | | 0.2 | | | |
| Cationic direct dye of formula (I31) | | | 0.15 | | |
| Cationic direct dye of formula $(IV)_{10}$ | | | | 0.12 | |
| Cationic direct dye of formula $(IV)_{27}$ | | | | | 0.10 |
| Triethanolamine cocoyl glutamate sold under the name ACYLGLUTAMATE CT12 by the company AJINOMOTO | 5.0 AS* | | | | |
| Sodium lauroyl sarcosinate sold under the name ORAMIX L30 by the company SEPPIC | | 5.0 AS* | | | |
| Sodium cocoyl isethionate sold under the name JORDAPON CI POWDER by the company PPG | | | 5.0 AS* | | |

-continued

|  | Example 1 | Example 2 | Example 3 | Example 4 | Example 5 |
|---|---|---|---|---|---|
| Lauryl ether carboxylic acid containing 10 EO sold under the name AKYPO RLM 100 by the company KAO |  |  |  | 5.0 AS* |  |
| Sodium salt of tartaric ester of cocoyl polyglucoside sold under the name GUCAROL AGE ET by the company CESALPINA |  |  |  |  | 5.0 AS* |
| Ethanol | 10 | 10 | 10 | 10 | 10 |
| 2-Amino-2-methyl-1-propanol qs | pH 9 | pH 9 | pH 9 | pH 9 | pH 9 |
| Demineralized water qs | 100 | 100 | 100 | 100 | 100 |

AS* denotes Active Substance

The above compositions were each applied for 30 minutes to locks of natural grey hair which is 90% white. The hair locks were then rinsed, washed with a standard shampoo and then dried.

The locks were dyed in the following shades:

| Examples | Shades obtained |
|---|---|
| 1 | dark red |
| 2 | dark orange |
| 3 | dark violet |
| 4 | dark red |
| 5 | dark purple |

What is claimed is:

1. A composition for dyeing keratinous fibers, comprising, in a medium suitable for dyeing,
(i) at least one cationic direct dye; and
(ii) at least one anionic surfactant;
wherein said at least one cationic direct dye is chosen from:
(A) compounds of formula (I) below:

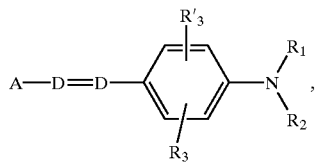

(I)

in which:
D is chosen from a nitrogen atom and a —CH group;
$R_1$ and $R_2$, which may be identical or different, are chosen from a hydrogen atom; $C_1$–$C_4$ alkyl radicals which may be unsubstituted or substituted with at least one radical chosen from a —CN radical, an —OH radical, and an —NH$_2$ radical; and a 4'-aminophneyl radical; or form, with each other or with a carbon atom of the benzene ring of formula (1), a heterocycle, which optionally contains an oxygen heteroatom or a nitrogen heteroatom and wherein said heterocycle may be unsubstituted or substituted with at least one radical chosen from $C_1$–$C_4$ radicals;

$R_3$ and $R'_3$, which may be identical or different, are chosen from a hydrogen atom, a chlorine atom, a bromine atom, an iodine atom, a fluorine atom, a cyano group, $C_1$–$C_4$ alkyl radicals, $C_1$–$C_4$ alkoxy radicals, and acetyloxy radicals;
X$^-$ is an anion;
A is chosen from structures $A_1$ to $A_{19}$ below:

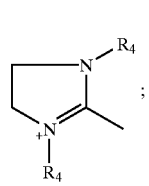

$A_1$

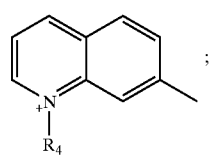

$A_2$

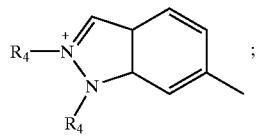

$A_3$

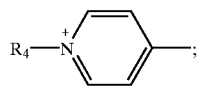

$A_4$

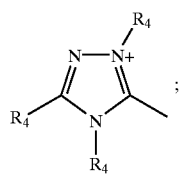

$A_5$

-continued

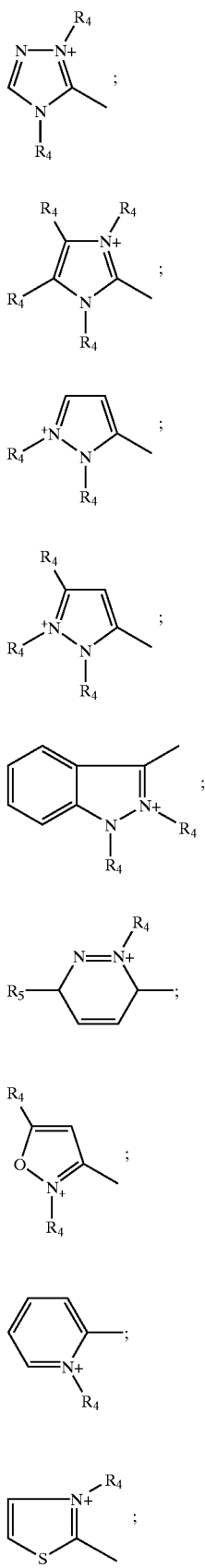

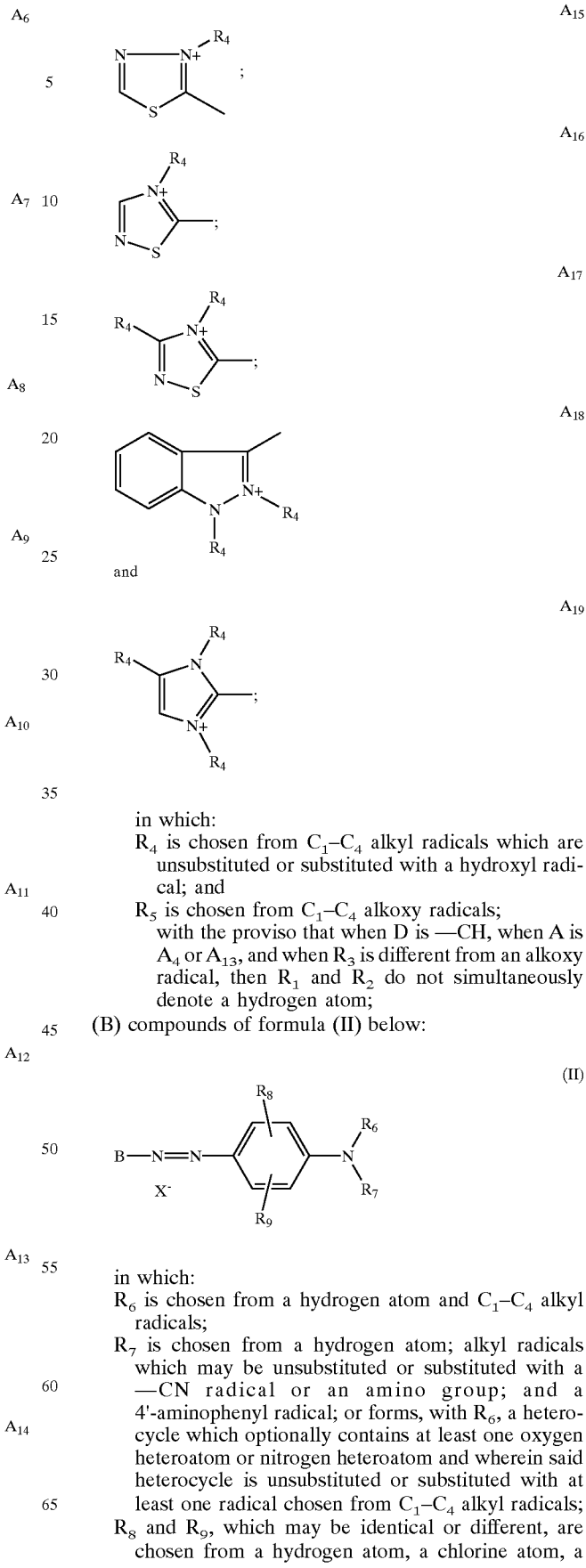

in which:
R₄ is chosen from $C_1$–$C_4$ alkyl radicals which are unsubstituted or substituted with a hydroxyl radical; and
R₅ is chosen from $C_1$–$C_4$ alkoxy radicals;
with the proviso that when D is —CH, when A is A₄ or A₁₃, and when R₃ is different from an alkoxy radical, then R₁ and R₂ do not simultaneously denote a hydrogen atom;

(B) compounds of formula (II) below:

in which:
R₆ is chosen from a hydrogen atom and $C_1$–$C_4$ alkyl radicals;
R₇ is chosen from a hydrogen atom; alkyl radicals which may be unsubstituted or substituted with a —CN radical or an amino group; and a 4'-aminophenyl radical; or forms, with R₆, a heterocycle which optionally contains at least one oxygen heteroatom or nitrogen heteroatom and wherein said heterocycle is unsubstituted or substituted with at least one radical chosen from $C_1$–$C_4$ alkyl radicals;
R₈ and R₉, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and a —CN radical;

$X^-$ is an anion;

B is chosen from structures B1 to B6 below:

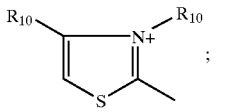
B1

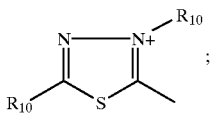
B2

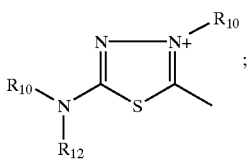
B3

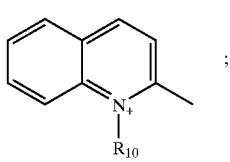
B4

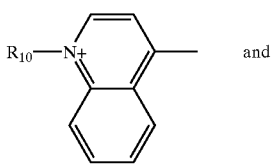
B5 and

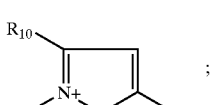
B6 in which:
$R_{10}$ is chosen from $C_1$–$C_4$ alkyl radicals;
$R_{11}$ and $R_{12}$, which may be identical or different, are chosen from a hydrogen atom and $C_1$–$C_4$ alkyl radicals;

(C) compounds of formulae (III) or (III') below:

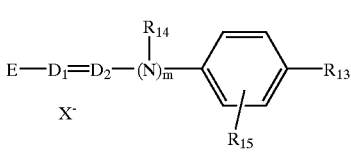
(III)

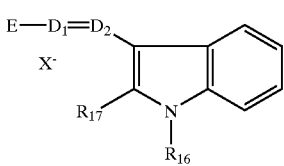
(III')

in which:
$R_{13}$ is chosen from a hydrogen atom, $C_1$–$C_4$ alkoxy radicals, a chlorine atom, a bromine atom, an iodine atom, a fluorine atom, and an amino radical;

$R_{14}$ is chosen from a hydrogen atom and $C_1$–$C_4$ alkyl radicals; or forms, with a carbon atom of the benzene ring, a heterocycle which optionally contains an oxygen heteroatom and wherein said heterocycle is unsubstituted or substituted with at least one $C_1$–$C_4$ alkyl group;

$R_{15}$ is chosen from a hydrogen atom, a chlorine atom, a bromine atom, an iodine atom, and a fluorine atom;

$R_{16}$ and $R_{17}$, which may be identical or different, are chosen from a hydrogen atom and $C_1$–$C_4$ alkyl radicals;

$D_1$ and $D_2$, which may be identical or different, are chosen from a nitrogen atom and a —CH group;

m is an integer that equals 0 or 1;

$X^-$ is an anion;

wherein, when $R_{13}$ is an unsubstituted amino group, then $D_1$ and $D_2$ simultaneously are a —CH group, and m is 0; and E is chosen from structures E1 to E8 below:

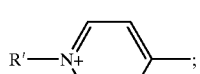
E1

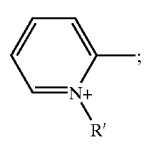
E2

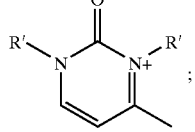
E3

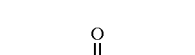

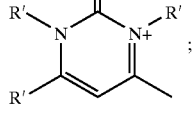
E4

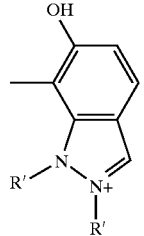
E5

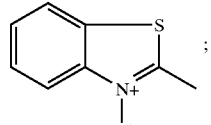
E6

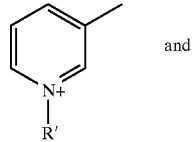
E7 and

-continued

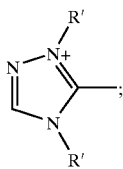

E8 in which
R' is chosen from $C_1$–$C_4$ alkyl radicals;
wherein, when m equals 0, and when $D_1$ is a nitrogen atom, then E may also be chosen from structure E9:

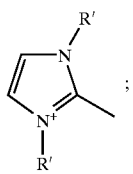

E9 in which:
R' is chosen from $C_1$–$C_4$ alkyl radicals; and (D) compounds of formula (IV) below:

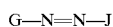

(IV)

in which:
G is a group chosen from structures $G_1$ to $G_3$:

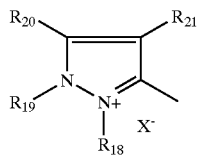

$G_1$

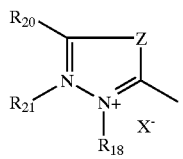

$G_2$

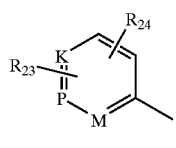

$G_3$ in which:
$R_{18}$ is chosen from $C_1$–$C_4$ alkyl radicals and a phenyl radical which is unsubstituted or substituted with at least one radical chosen from $C_1$–$C_4$ alkyl radicals, a fluorine atom, a bromine atom, a chlorine atom, and an iodine atom;
$R_{19}$ is chosen from $C_1$–$C_4$ alkyl radicals and a phenyl radical;
$R_{20}$ and $R_{21}$, which may be identical or different, are chosen from $C_1$–$C_4$ alkyl radicals and a phenyl radical; or form, together in $G_1$, a benzene ring which is substituted with at least one radical chosen from $C_1$–$C_4$ alkyl radicals, $C_1$–$C_4$ alkoxy radicals, and a $NO_2$ radical; or form, together in $G_2$, a benzene ring which is unsubstituted or substituted with at least one radical chosen from $C_1$–$C_4$ alkyl radicals, $C_1$–$C_4$ alkoxy radicals, and $NO_2$ radicals; and $R_{20}$ may also be chosen from a hydrogen atom;
Z is chosen from an oxygen atom, a sulphur atom, and —$NR_{19}$ radicals;
M, K, and P, each independently of the other, are chosen from —CH, —C($C_1$–$C_4$alkyl), and —$NR_{22}(X^-)_r$; r is 0 or 1;
$R_{22}$ is chosen from an $O^-$ atom, $C_1$–$C_4$ alkoxy radicals, and $C_1$–$C_4$ alkyl radicals;
$R_{23}$ and $R_{24}$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and an —$NO_2$ radical;
$X^-$ is an anion;
wherein J is chosen from:
(a) structures of $J_1$ below:

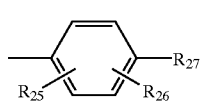

$J_1$ in which:
$R_{25}$ is chosen from a hydrogen atom, a chlorine atom, a bromine atom, an iodine atom, a fluorine atom, $C_1$–$C_4$ alkyl radicals, $C_1$–$C_4$ alkoxy radicals, an —OH radical, a —$NO_2$ radical, —$NHR_{28}$ radicals, —$NR_{29}R_{30}$ radicals, and —NHCO($C_1$–$C_4$ alkyl) radicals; or forms, with $R_{26}$, a 5- or 6-member ring which optionally contains at least one heteroatom chosen from an oxygen atom, a nitrogen atom, and a sulfur atom;
$R_{26}$ is chosen from a hydrogen atom, a chlorine atom, a bromine atom, an iodine atom, a fluorine atom, $C_1$–$C_4$ alkyl radicals, and $C_1$–$C_4$ alkoxy radicals; or forms, with $R_{27}$ or $R_{28}$, a 5- or 6-member ring which optionally contains at least one heteroatom chosen from an oxygen atom, a nitrogen atom, and a sulfur atom;
$R_{27}$ is chosen from a hydrogen atom, an —OH radical, —$NHR_{28}$ radicals, and —$NR_{29}R_{30}$ radicals;
$R_{28}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, and a phenyl radical; and
$R_{29}$ and $R_{30}$, which may be identical or different, are chosen from $C_1$–$C_4$ alkyl radicals, $C_1$–$C_4$ monohydroxyalkyl radicals, and $C_2C_4$ polyhydroxyalkyl radicals; and (b) wherein J is further chosen from 5- and 6- member nitrogen-containing heterocycle groups which optionally contain at least one heteroatom and/or at least one carbonyl-containing group and wherein said heterocycle may be substituted or unsubstituted with at least one substituent chosen from $C_1$–$C_4$ alkyl radicals, an amino radical, and a phenyl radical; and wherein said at least one anionic surfactant is chosen from:
(ii)$_1$—polyoxyethylenated ether carboxylic acids and salts thereof;
(ii)$_2$—fatty glucamide sulphates;
(ii)$_3$—alkyl galactoside uronates; and
(ii)$_4$—anionic derivatives of alkyl polyglucosides.

2. A composition according to claim 1, wherein said keratinous fibers are chosen from human keratinous fibers.

3. A composition according to claim 1, wherein said keratinous fibers are hairs.

4. A composition according to claim 1, wherein, in the definition of compounds of formula (I), (II), (III), and (III'), said anions X⁻ are chosen from chloride, methyl sulphate, and acetate.

5. A composition according to claim 1, wherein, in the definition of compounds of formula (IV), X⁻ is chosen from chloride, iodide, methylsulphate, ethylsulphate, acetate, and perchlorate.

6. A composition according to claim 1, wherein, in the definition of J, said 5- and 6-member nitrogen-containing heterocycle groups are chosen from structure $J_2$ below:

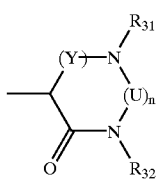

in which:

$R_{31}$, and $R_{32}$, which may be identical or different, are chosen from a hydrogen atom, $C_1$–$C_4$ alkyl radicals, and a phenyl radical;

Y is chosen from a —CO— radical and the radical

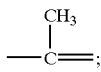

and n equals 0 or 1;

wherein when n equals 1, then U is a —CO— radical.

7. A composition according to claim 1, wherein the compounds of formula (I) are chosen from structures (I1) to (I54) below:

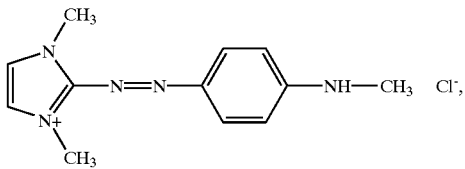

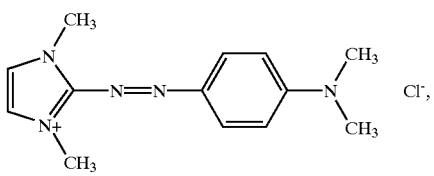

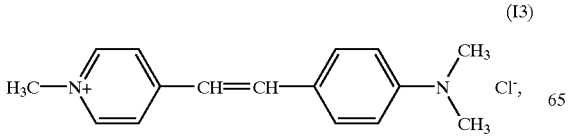

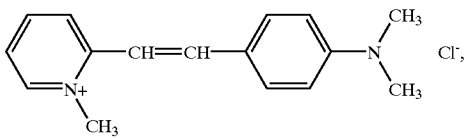

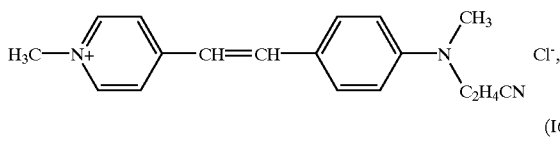

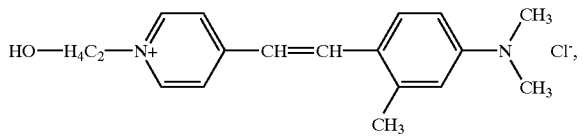

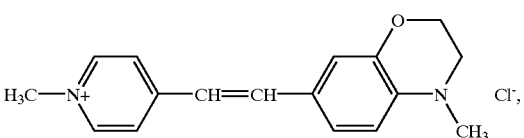

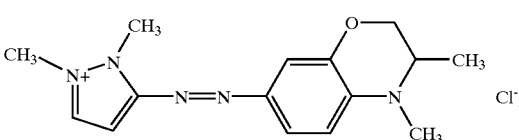

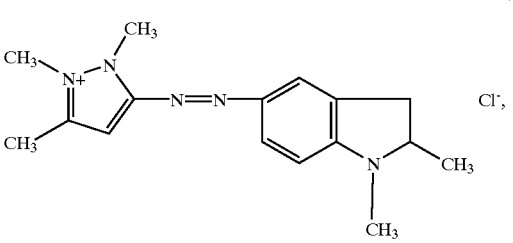

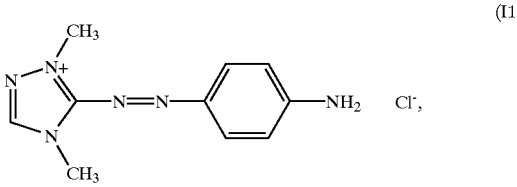

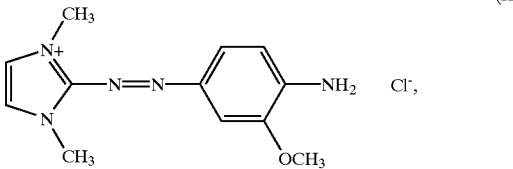

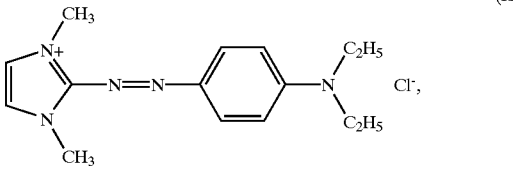

-continued (I13), (I14), (I15), (I16), (I17), (I18), (I19), (I20), (I21), (I22), (I23), (I24), (I25), (I26), (I27), (I28), (I29)

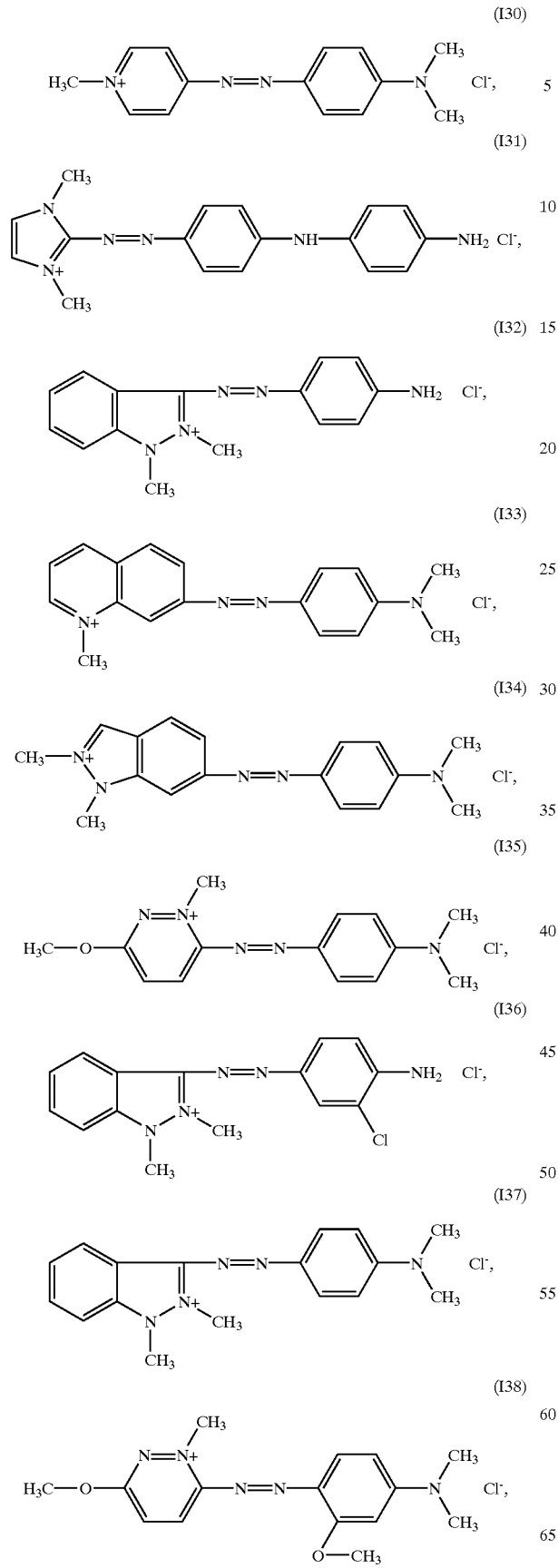
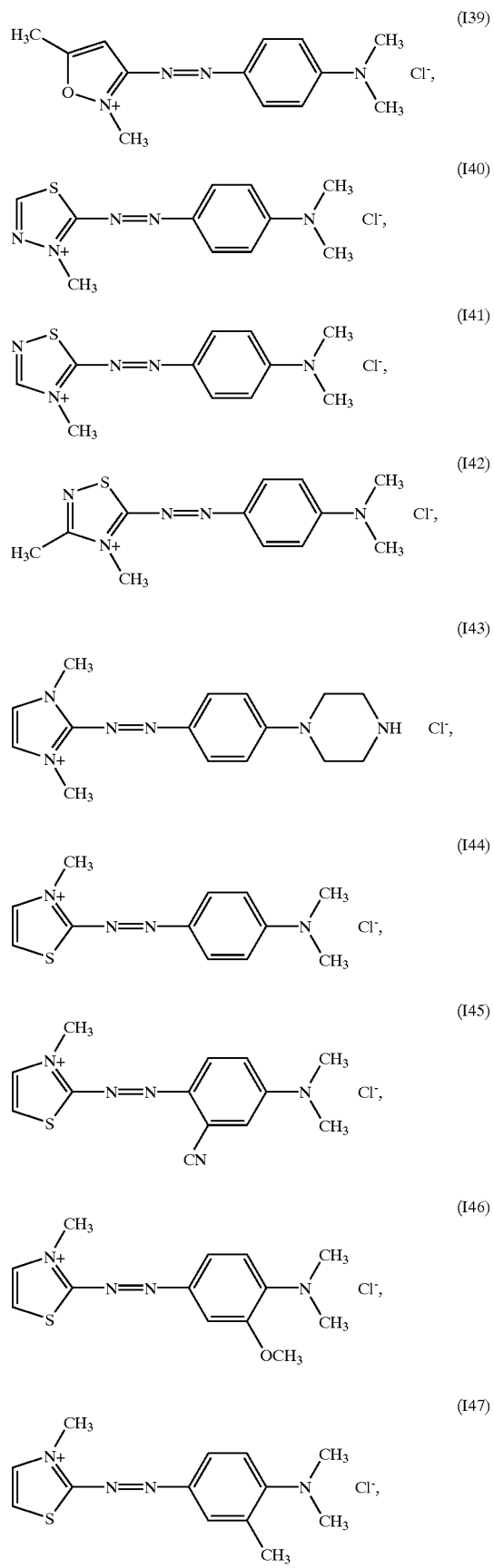

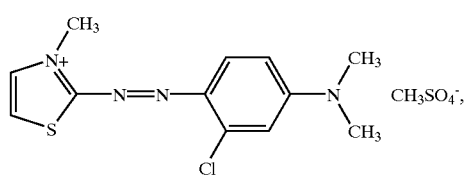 (I48)

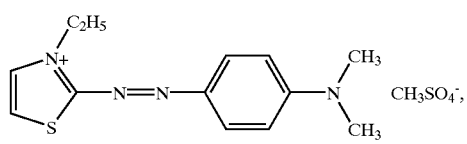 (I49)

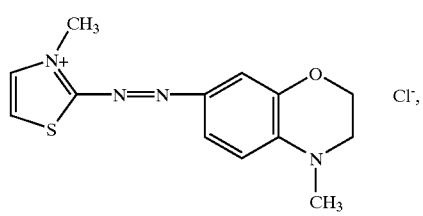 (I50)

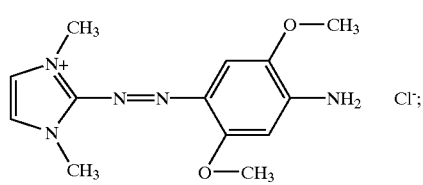 (I51)

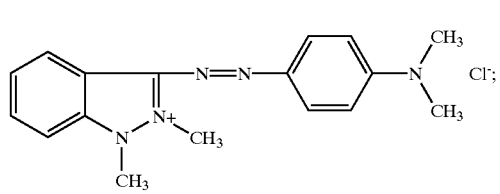 (I52)

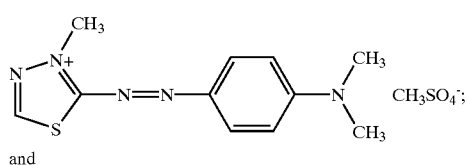 (I53)

and

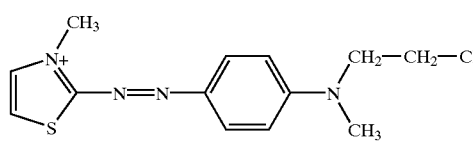 (I54)

8. A composition according to claim 7, wherein the compounds of formula (I) are chosen form chosen from structures (I1), (I2), (I14), and (I31).

9. A composition according to claim 1, wherein the compounds of formula (II) are chosen from structures (II1) to (II9) below:

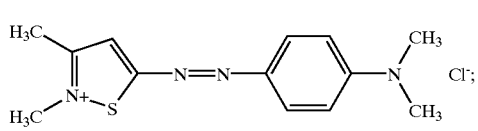 (II1)

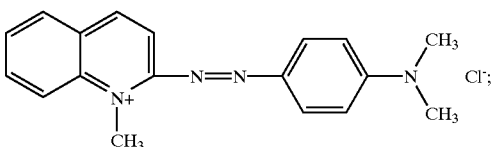 (II2)

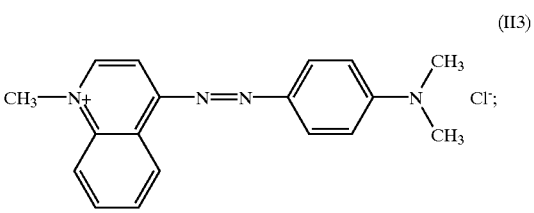 (II3)

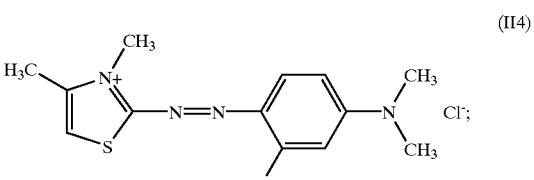 (II4)

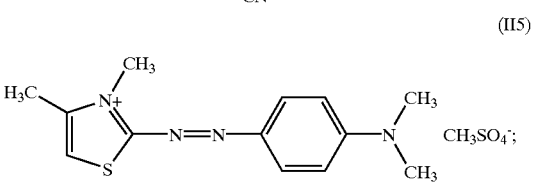 (II5)

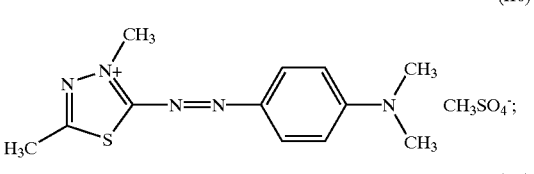 (II6)

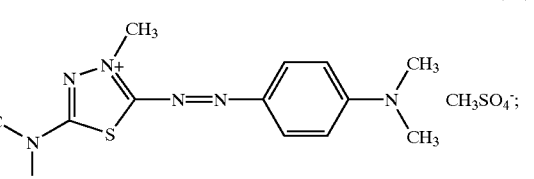 (II7)

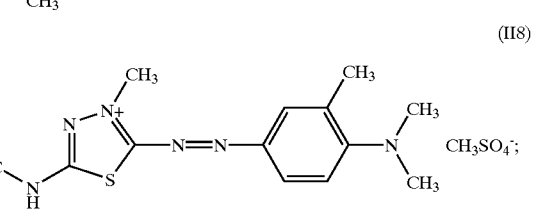 (II8)

and

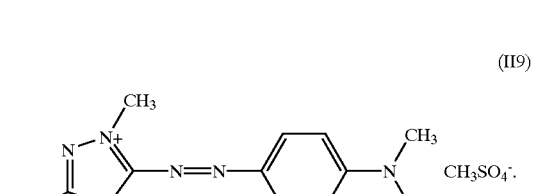 (II9)

10. A composition according to claim 1, wherein the compounds of formula (III) are chosen from structures (III1) to (III18):

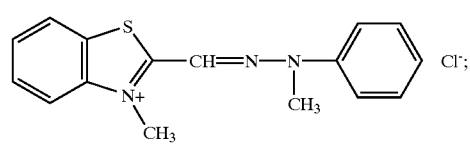
(III1)
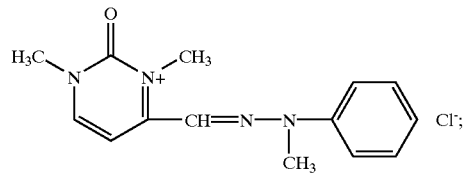
(III2)
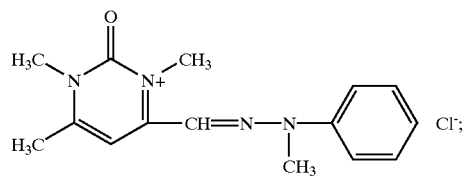
(III3)
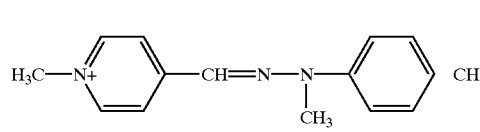
(III4)
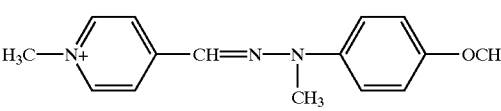
(III5)
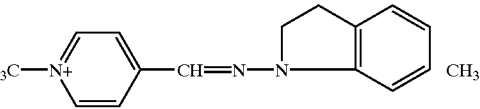
(III6)
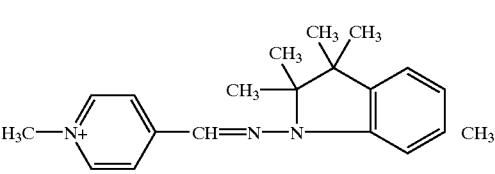
(III7)
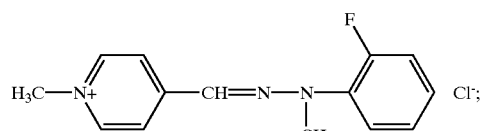
(III8)
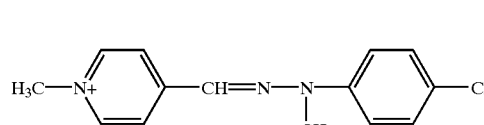
(III9)
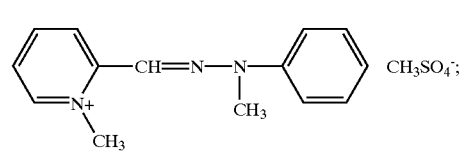
(III10)
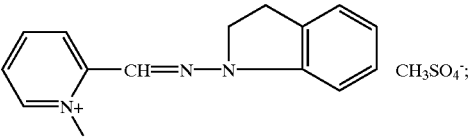
(III11)
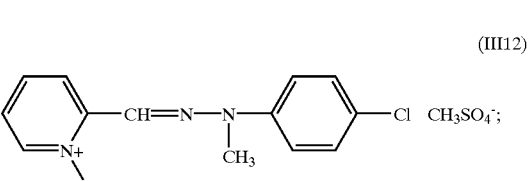
(III12)
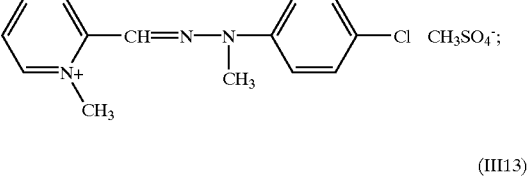
(III13)
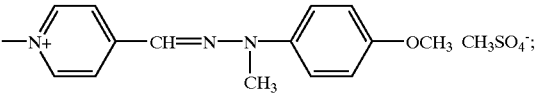
(III14)
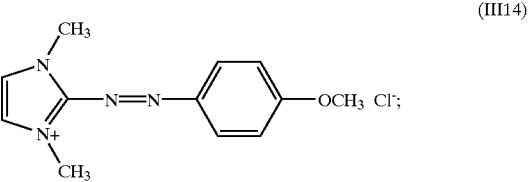
(III15)
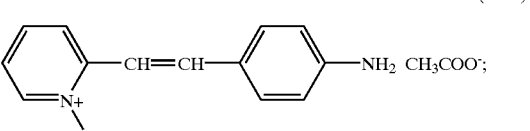
(III16)
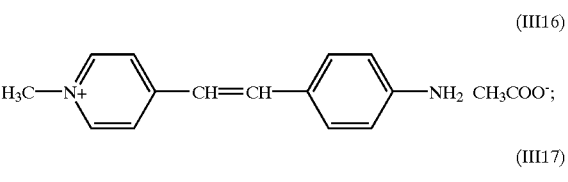
(III17)
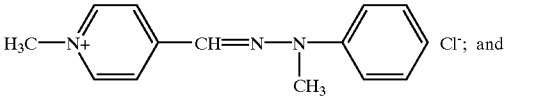
(III18)
11. A composition according to claim 10, wherein the compounds of formula (III) are chosen from structures (III4), (III5) and (III13).
12. A composition according to claim 1, wherein the compounds of formula (III') are chosen from structures (III'1) to (III'3):

13. A composition according to claim 1, wherein the compounds of formula (IV) are chosen from structures $(IV)_1$ to $(IV)_{77}$:

-continued (IV)₁₄ — (IV)₃₀: chemical structures not transcribed.

-continued (IV)₃₁: 2-[(4-diethylamino)phenylazo]-1-methylpyridinium methylsulfate (IV)₃₂: 2-[(4-dimethylamino)phenylazo]-1,3-dimethylpyridinium methylsulfate (IV)₃₃: 2-[(2-chloro-4-dimethylamino)phenylazo]-1-methylpyridinium methylsulfate (IV)₃₄: 2-[(4-phenylamino)phenylazo]-1,6-dimethylpyridinium methylsulfate (IV)₃₅: 2-[(4-dimethylamino)phenylazo]-1,5-dimethylpyridinium methylsulfate (IV)₃₆: 2-[(2-acetylamino-4-dimethylamino)phenylazo]-1-methylpyridinium methylsulfate (IV)₃₇: 3-[(4-dimethylamino)phenylazo]-1-methylpyridinium methylsulfate (IV)₃₈: 5-[(4-dimethylamino)phenylazo]-1,2-dimethylpyridinium methylsulfate (IV)₃₉: 3-[(4-dimethylamino-2-methyl)phenylazo]-1-ethylpyridinium ethylsulfate (IV)₄₀: 3-[(2-chloro-4-dimethylamino)phenylazo]-1-methylpyridinium methylsulfate (IV)₄₁: 3-[(4-phenylamino)phenylazo]-1-methylpyridinium methylsulfate (IV)₄₂: 3-[(2-acetylamino-4-dimethylamino)phenylazo]-1-ethylpyridinium ethylsulfate (IV)₄₃: 3-[(4-dimethylamino-2-methyl)phenylazo]-1-butylpyridinium bromide (IV)₄₄: pyrazolone azo derivative, methylsulfate (IV)₄₅: barbituric acid azo pyridine N-oxide derivative (IV)₄₆
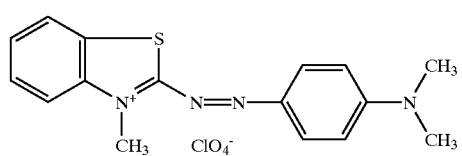
(IV)₅₄
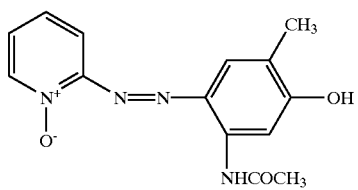
(IV)₄₇
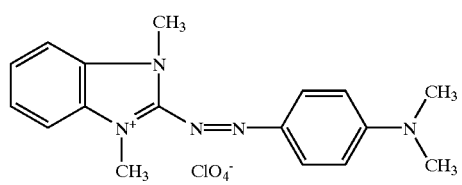
(IV)₅₅
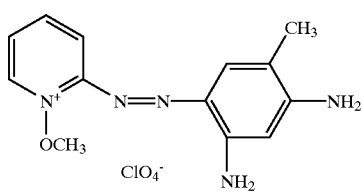
(IV)₄₈
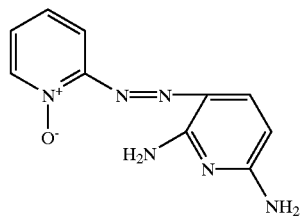
(IV)₅₆
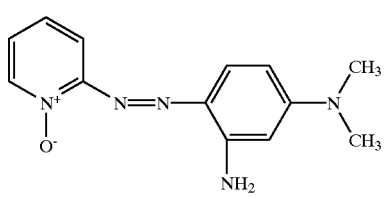
(IV)₄₉
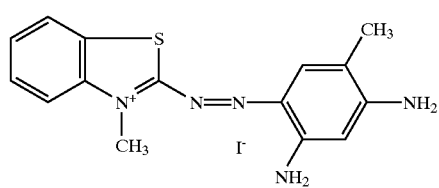
(IV)₅₇
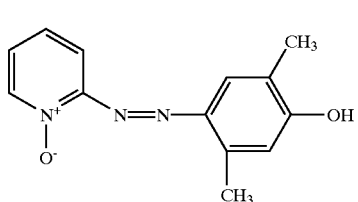
(IV)₅₀
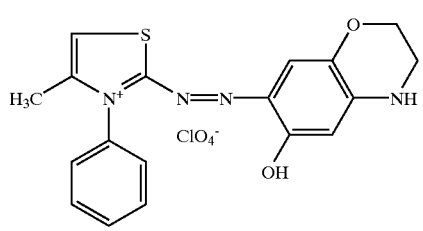
(IV)₅₈
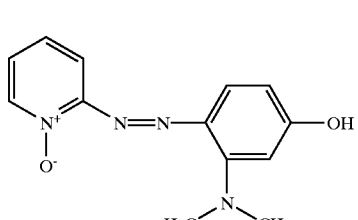
(IV)₅₁
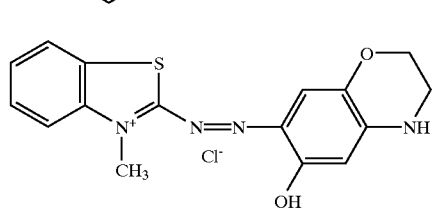
(IV)₅₉
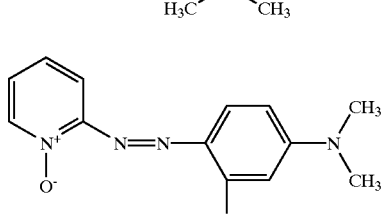
(IV)₅₂
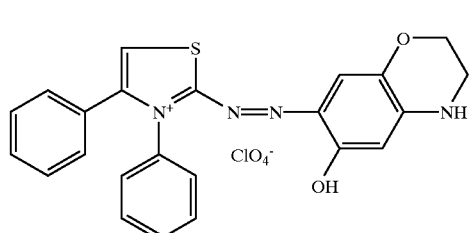
(IV)₆₀
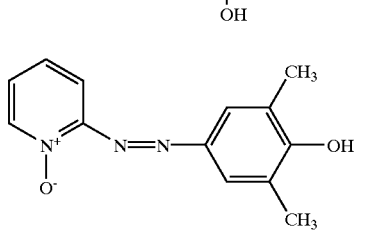
(IV)₅₃
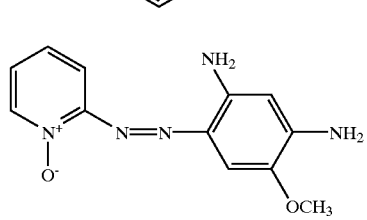
(IV)₆₁
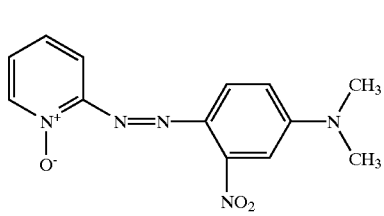

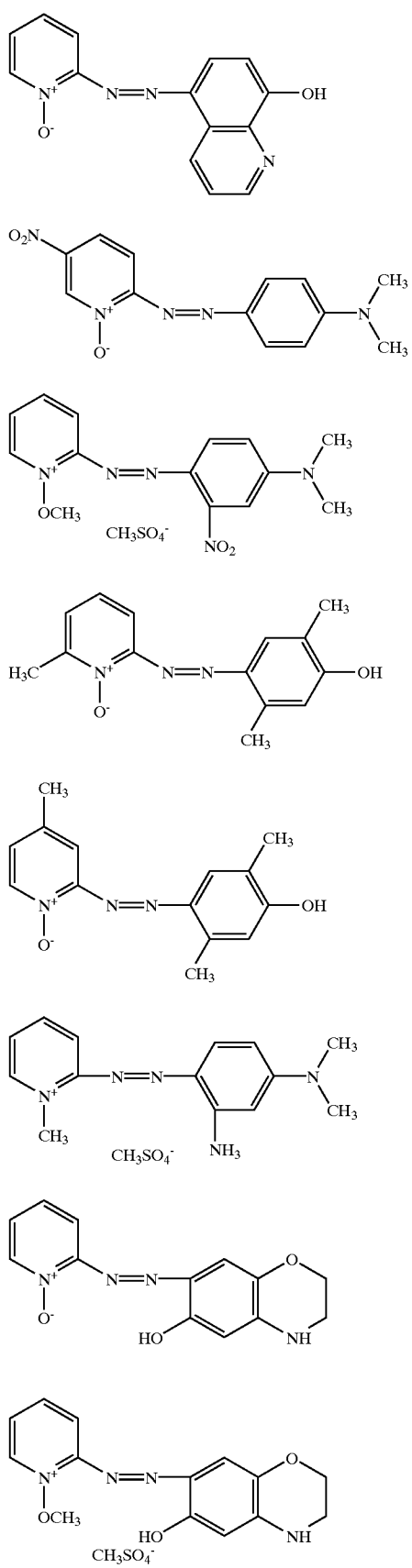
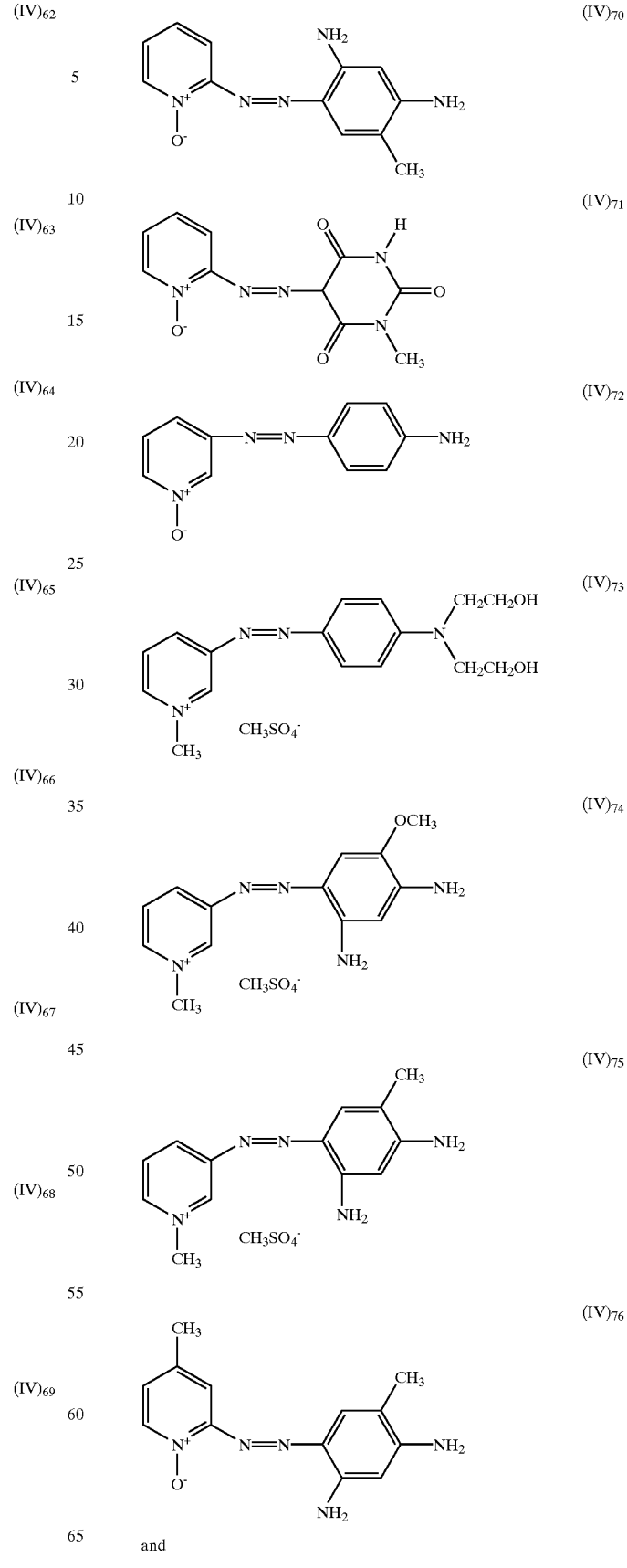
and

-continued

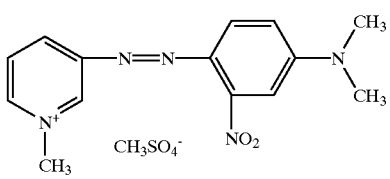
(IV)₇₇

14. A composition according to claim 1, wherein said at least one cationic direct dye is present in an amount ranging from 0.001 to 10 percent by weight of the total weight of said composition.

15. A composition according to claim 14, wherein said amount ranges from 0.005 to 5 percent.

16. A composition according to claim 1, wherein said at least one anionic surfactant is chosen from (ii)₆—polyoxyalkylenated ether carboxylic acids and salts thereof and contains from 2 to 50 ethylene oxide groups.

17. A composition according to claim 16, wherein said (ii)₆—polyoxyalkylenated ether carboxylic acids and salts thereof are represented by formula (VII) below:

$$R^6(-OC_2H_4)_nOCH_2COOA \quad (VII)$$

in which:
 $R^6$ is chosen from $C_6$–$C_{20}$ alkyl groups and ($C_6$–$C_{20}$) alkylaryl groups;
 n is an integer or a decimal number, wherein the mean value of n ranges from 2 to 24; and
 A is chosen from H, ammonium, Na, K, Li, Mg, a monoethanolamine residue, and a triethanolamine residue.

18. A composition according to claim 17, wherein the mean value of n ranges from 3 to 10.

19. A composition according to claim 17, wherein, in the definition of $R^6$, said ($C_6$–$C_{20}$)alkylaryl groups are chosen from ($C_6$–$C_{20}$)alkylphenyl groups.

20. A composition according to claim 1, wherein said at least one anionic surfactant chosen from (ii)₉—anionic compounds of alkyl polyglucoside are chosen from:
 alkyl polyglucoside sulphates;
 alkyl polyglucoside sulphonates;
 alkyl polyglucoside ether carboxylates;
 alkyl polyglucoside sulphosuccinates;
 alkyl polyglucoside isethionates; and
 alkyl polyglucoside phosphates.

21. A composition according to claim 1, wherein said at least one anionic surfactant is present in an amount ranging from 0.05 to 30 percent by weight of the total weight of said composition.

22. A composition according to claim 21, wherein said amount ranges from 0.1 to 15 percent.

23. A composition according to claim 1, wherein said medium suitable for dyeing is water or a mixture of water and at least one organic solvent.

24. A composition according to claim 1, wherein said composition has a pH having a value ranging from 2 to 11.

25. A composition according to claim 24, wherein said value ranges from 5 to 10.

26. A composition according to claim 1, wherein said composition further comprising at least one oxidation base chosen from the para-phenylenediamines, bisphenylalkylenediamines, para-aminophenols, ortho-aminophenols, and heterocyclic bases.

27. A composition according to claim 26, wherein said at least one oxidation base is present in an amount ranging from 0.0005 to 12 percent by weight of the total weight of said composition.

28. A composition according to claim 27, wherein said amount ranges from 0.005 to 6 percent.

29. A composition according to claim 26, further comprising at least one coupler chosen from meta-phenylenediamines, meta-aminophenols, meta-diphenols, and the heterocyclic couplers.

30. A composition according to claim 29, wherein said at least one coupler is present in an amount ranging from 0.0001 to 10 percent by weight of the total weight of said composition.

31. A composition according to claim 30, wherein said amount ranges from 0.005 to 5 percent.

32. A composition according to claim 29, further comprising at least one oxidizing agent.

33. A method for dyeing keratinous fibers, comprising applying to said keratinous fibers for a time sufficient to develop a desired coloration, a composition comprising, in a medium suitable for dyeing,
 (i) at least one cationic direct dye; and
 (ii) at least one anionic surfactant;
 wherein said at least one cationic direct dye is chosen from:
 (A) compounds of formula (I) below:

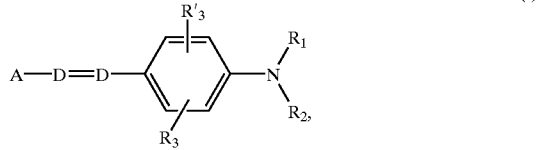
(I)

in which:
 D is chosen from a nitrogen atom and a —CH group;
 $R_1$ and $R_2$, which may be identical or different, are chosen from a hydrogen atom; $C_1$–$C_4$ alkyl radicals which may be unsubstituted or substituted with at least one radical chosen from a —CN radical, an —OH radical, and an —NH₂ radical; and a 4'-aminophenyl radical; or form, with each other or with a carbon atom of the benzene ring of formula (I), a heterocycle, which optionally contains an oxygen heteroatom or a nitrogen heteroatom and wherein said heterocycle may be unsubstituted or substituted with at least one radical chosen from $C_1$–$C_4$ radicals;
 $R_3$ and $R'_3$, which may be identical or different, are chosen from a hydrogen atom, a chlorine atom, a bromine atom, an iodine atom, a fluorine atom, a cyano group, $C_1$–$C_4$ alkyl radicals, $C_1$–$C_4$ alkoxy radicals, and acetyloxy radicals;
 $X^-$ is an anion;
 A is chosen from structures $A_1$ to $A_{19}$ below:

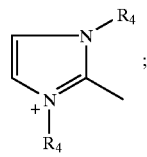
$A_1$

-continued

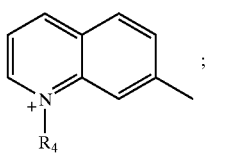 A₂

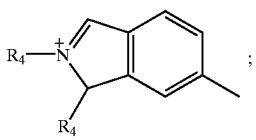 A₃

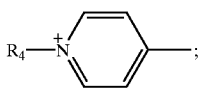 A₄

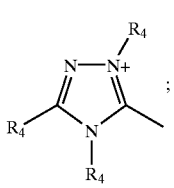 A₅

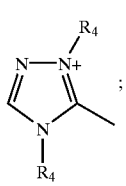 A₆

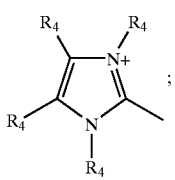 A₇

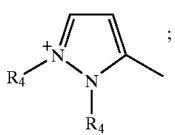 A₈

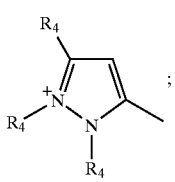 A₉

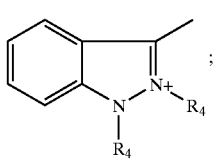 A₁₀

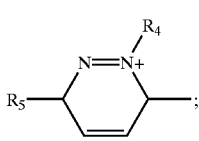 A₁₁

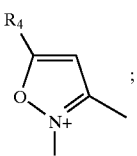 A₁₂

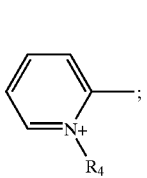 A₁₃

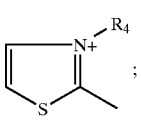 A₁₄

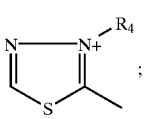 A₁₅

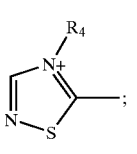 A₁₆

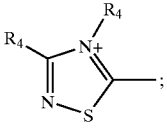 A₁₇

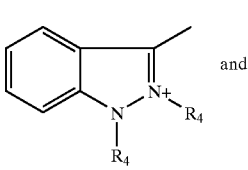 and A₁₈

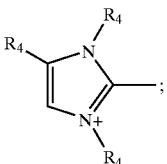 A₁₉ in which:

$R_4$ is chosen from $C_1$–$C_4$ alkyl radicals which are unsubstituted or substituted with a hydroxyl radical; and $R_5$ is chosen from $C_1$–$C_4$ alkoxy radicals;

with the proviso that when D is —CH, when A is $A_4$ or $A_{13}$, and when $R_3$ is different from an alkoxy radical, then $R_1$ and $R_2$ do not simultaneously denote a hydrogen atom;

(B) compounds of formula (II) below:

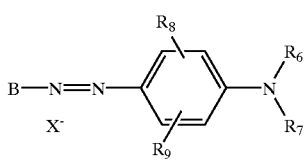
(II)

in which:
- $R_6$ is chosen from a hydrogen atom and $C_1$–$C_4$ alkyl radicals;
- $R_7$ is chosen from a hydrogen atom; alkyl radicals which may be unsubstituted or substituted with a —CN radical or an amino group; and a 4'-aminophenyl radical; or forms, with $R_6$, a heterocycle which optionally contains at least one oxygen heteroatom or nitrogen heteroatom and wherein said heterocycle is unsubstituted or substituted with at least one radical chosen from $C_1$–$C_4$ alkyl radicals;
- $R_8$ and $R_9$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and a —CN radical;
- $X^-$ is an anion;
- B is chosen from structures B1 to B6 below:

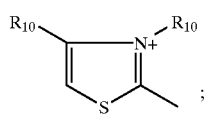
B1

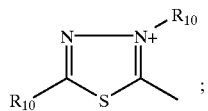
B2

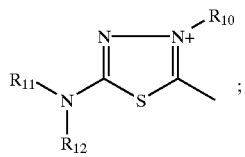
B3

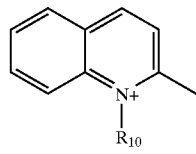
B4

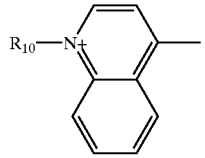
B5 and

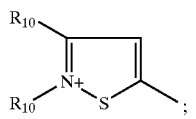
B6 in which:
- $R_{10}$ is chosen from $C_1$–$C_4$ alkyl radicals;
- $R_{11}$ and $R_{12}$, which may be identical or different, are chosen from a hydrogen atom and $C_1$–$C_4$ alkyl radicals;

(C) compounds of formulae (III) or (III') below:

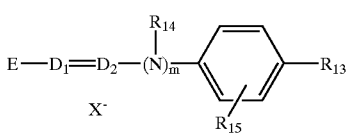
(III)

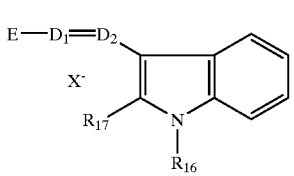
(III')

in which:
- $R_{13}$ is chosen from a hydrogen atom, $C_1$–$C_4$ alkoxy radicals, a chlorine atom, a bromine atom, an iodine atom, a fluorine atom, and an amino radical;
- $R_{14}$ is chosen from a hydrogen atom and $C_1$–$C_4$ alkyl radicals; or forms, with a carbon atom of the benzene ring, a heterocycle which optionally contains an oxygen heteroatom and wherein said heterocycle is unsubstituted or substituted with at least one $C_1$–$C_4$ alkyl group;
- $R_{15}$ is chosen from a hydrogen atom, a chlorine atom, a bromine atom, an iodine atom, and a fluorine atom;
- $R_{16}$ and $R_{17}$, which may be identical or different, are chosen from a hydrogen atom and $C_1$–$C_4$ alkyl radicals;
- $D_1$ and $D_2$, which may be identical or different, are chosen from a nitrogen atom and a —CH group;
- m is an integer that equals 0 or 1;
- $X^-$ is an anion;
- wherein, when $R_{13}$ is an unsubstituted amino group, then $D_1$ and $D_2$ simultaneously are a —CH group, and m is 0; and
- E is chosen from structures E1 to E8 below:

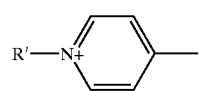
E1

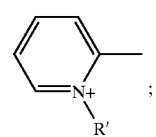
E2

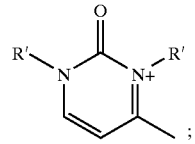
E3

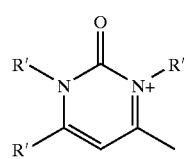
E4

-continued

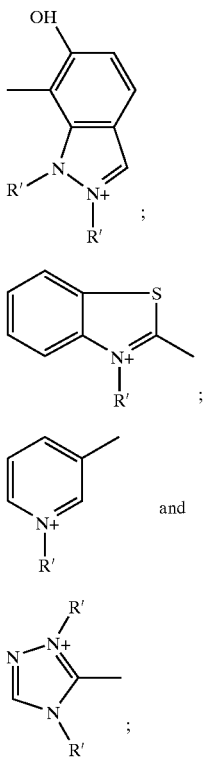

E5

E6

E7 and

E8 in which

R' is chosen from $C_1$–$C_4$ alkyl radicals;

wherein, when m equals 0, and when $D_1$ is a nitrogen atom, then E may also be chosen from structure E9:

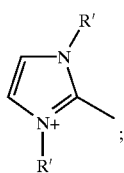

E9 in which:

R' is chosen from $C_1$–$C_4$ alkyl radicals; and (D) compounds of formula (IV) below:

G—N=N—J (IV)

in which:

G is a group chosen from structures $G_1$ to $G_3$:

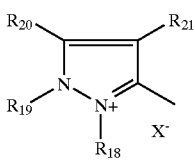

$G_1$

-continued

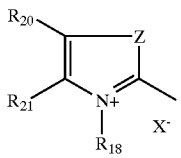

$G_2$

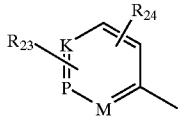

$G_3$ in which:

$R_{18}$ is chosen from $C_1$–$C_4$ alkyl radicals and a phenyl radical which is unsubstituted or substituted with at least one radical chosen from $C_1$–$C_4$ alkyl radicals, a fluorine atom, a bromine atom, a chlorine atom, and an iodine atom;

$R_{19}$ is chosen from $C_1$–$C_4$ alkyl radicals and a phenyl radical;

$R_{20}$ and $R_{21}$, which may be identical or different, are chosen from $C_1$–$C_4$ alkyl radicals and a phenyl radical; or form, together in $G_1$, a benzene ring which is substituted with at least one radical chosen from $C_1$–$C_4$ alkyl radicals, $C_1$–$C_4$ alkoxy radicals, and a $NO_2$ radical; or form, together in $G_2$, a benzene ring which is unsubstituted or substituted with at least one radical chosen from $C_1$–$C_4$ alkyl radicals, $C_1$–$C_4$ alkoxy radicals, and $NO_2$ radicals; and $R_{20}$ may also be chosen from a hydrogen atom;

Z is chosen from an oxygen atom, a sulphur atom, and —$NR_{19}$ radicals;

M, K, and P, each independently of the other, are chosen from —CH, —C($C_1$–$C_4$alkyl), and —$NR_{22}(X^-)_r$; r is 0 or 1;

$R_{22}$ is chosen from an $O^-$ atom, $C_1$–$C_4$ alkoxy radicals, and $C_1$–$C_4$ alkyl radicals;

$R_{23}$ and $R_{24}$, which may be identical or different, are chosen from a hydrogen atom, a chlorine atom, a bromine atom, an iodine atom, a fluorine atom, $C_1C_4$ alkyl radicals, $C_1$–$C_4$ alkoxy radicals, and an —$NO_2$ radical;

$X^-$ is an anion;

wherein J is chosen from:

(a) structures of $J_1$ below:

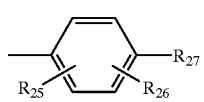

$J_1$ in which:

$R_{25}$ is chosen from a hydrogen atom, a chlorine atom, a bromine atom, an iodine atom, a fluorine atom, $C_1$–$C_4$ alkyl radicals, $C_1$–$C_4$ alkoxy radicals, an —OH radical, a —$NO_2$ radical, —NHR28 radicals, —$NR_{29}R_{30}$ radicals, and —NHCO($C_1$–$C_4$ alkyl) radicals; or forms, with $R_{26}$, a 5- or 6-member ring which optionally contains at least one heteroatom chosen from an oxygen atom, a nitrogen atom, and a sulfur atom;

$R_{26}$ is chosen from a hydrogen atom, a chlorine atom, a bromine atom, an iodine atom, a fluorine atom, C₁–C₄ alkyl radicals, and C₁–C₄ alkoxy radicals; or forms, with R₂₇ or R₂₈, a 5- or 6-member ring which optionally contains at least one heteroatom chosen from an oxygen atom, a nitrogen atom, and a sulfur atom;

R₂₇ is chosen from a hydrogen atom, an —OH radical, —NHR₂₈ radicals, and —NR₂₉R₃₀ radicals;

R₂₈ is chosen from a hydrogen atom, C₁–C₄ alkyl radicals, C₁–C₄ monohydroxyalkyl radicals, C₂–C₄ polyhydroxyalkyl radicals, and a phenyl radical; and R₂₉ and R₃₀, which may be identical or different, are chosen from C₁–C₄ alkyl radicals, C₁–C₄ monohydroxyalkyl radicals, and C₂–C₄ olyhydroxyalkyl radicals; and (b) wherein J is further chosen from 5- and 6-member nitrogen-containing heterocycle groups which optionally contain at least one heteroatom and/or at least one carbonyl-containing group and wherein said heterocycle may be substituted or unsubstituted with at least one substituent chosen from C₁–C₄ alkyl radicals, an amino radical, and a phenyl radical; and wherein said at least one anionic surfactant is chosen from:

(ii)₁—polyoxyethylenated ether carboxylic acids and salts thereof;

(ii)₂—fatty glucamide sulphates;

(ii)₃—alkyl galactoside uronates; and (ii)₄—anionic derivatives of alkyl polyglucosides.

34. A method according to claim 33, wherein said keratinous fibers are chosen from human keratinous fibers.

35. A method according to claim 34, wherein said human keratinous fibers are hairs.

36. A method according to claim 33, further comprising thereafter rinsing said keratinous fibers after applying said composition thereon.

37. A method according to claim 36, further comprising washing said keratinous fibers with a shampoo after said rinsing.

38. A method according to claim 37, further comprising rinsing again said keratinous fibers after said washing.

39. A method according to claim 38, further comprising drying said keratinous fibers.

40. A method for dyeing keratinous fibers, comprising:

separately storing a first composition and a second composition;

mixing said first composition with said second composition before applying the resultant mixture to said keratinous fibers; and applying said mixture to said keratinous fibers;

wherein said first composition comprises, in a medium suitable for dyeing, at least one cationic direct dye and at least one oxidation base;

wherein said second composition comprises, in a medium suitable for dyeing, at least one oxidizing agent;

wherein either said first composition or said second composition comprises at least one anionic surfactant chosen from:

(ii)₁—polyoxyethylenated ether carboxylic acids and salts thereof;

(ii)₂—fatty glucamide sulphates;

(ii)₁—alkyl galactoside uronates; and (ii)₂—anionic derivatives of alkyl polyglucosides;

wherein said at least one cationic direct dye is chosen from:

(A) compounds of formula (I) below:

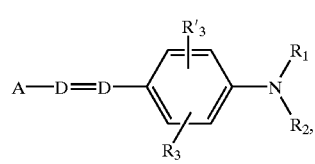

in which:

D is chosen from a nitrogen atom and a —CH group;

R₁ and R₂, which may be identical or different, are chosen from a hydrogen atom; C₁–C₄ alkyl radicals which may be unsubstituted or substituted with at least one radical chosen from a —CN radical, an —OH radical, and an —NH₂ radical; and a 4'-aminophenyl radical; or form, with each other or with a carbon atom of the benzene ring of formula (I), a heterocycle, which optionally contains an oxygen heteroatom or a nitrogen heteroatom and wherein said heterocycle may be unsubstituted or substituted with at least one radical chosen from C₁–C₄ radicals;

R₃ and R'₃, which may be identical or different, are chosen from a hydrogen atom, a chlorine atom, a bromine atom, an iodine atom, a fluorine atom, a cyano group, C₁–C₄ alkyl radicals, C₁–C₄ alkoxy radicals, and acetyloxy radicals;

X⁻ is an anion;

A is chosen from structures A₁ to A₁₉ below:

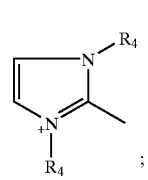

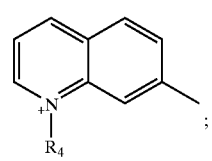

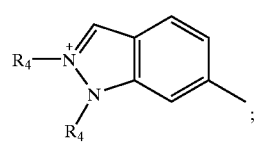

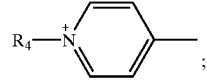

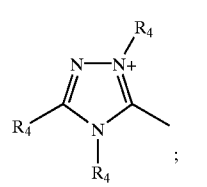

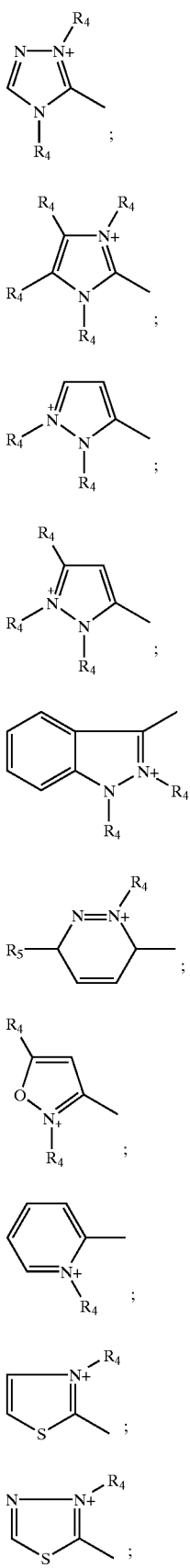

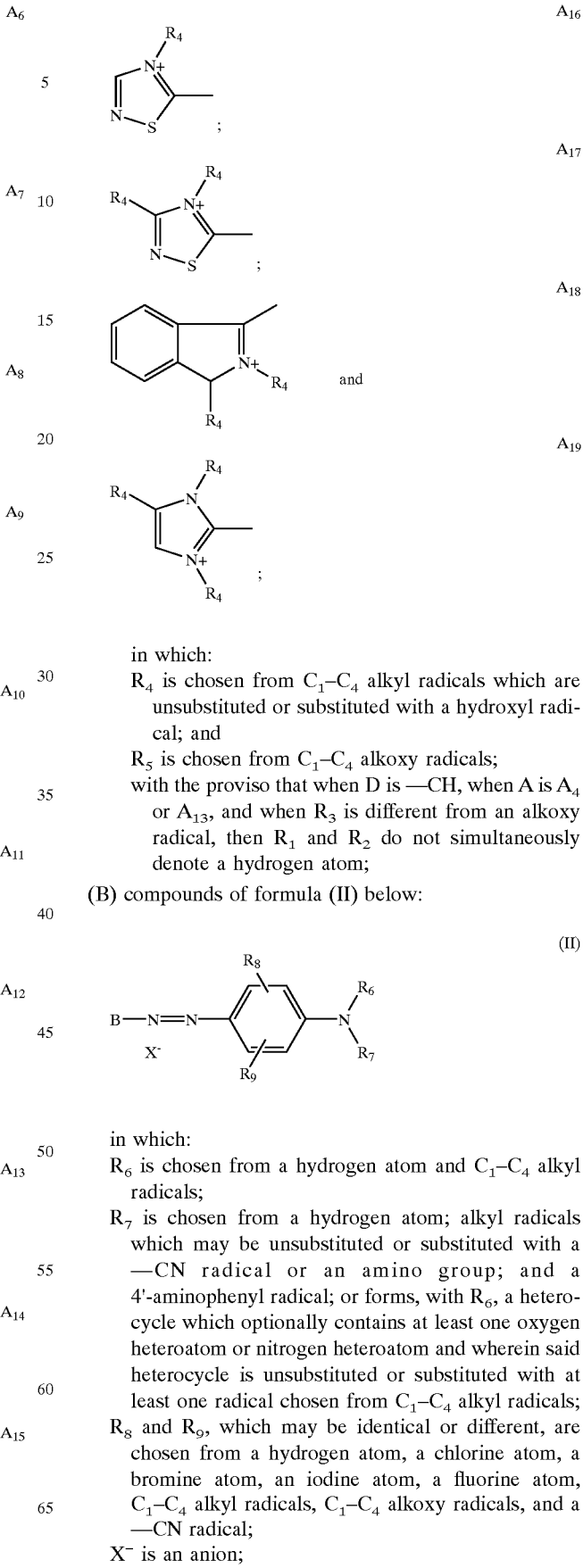

in which:
R$_4$ is chosen from C$_1$–C$_4$ alkyl radicals which are unsubstituted or substituted with a hydroxyl radical; and
R$_5$ is chosen from C$_1$–C$_4$ alkoxy radicals;
with the proviso that when D is —CH, when A is A$_4$ or A$_{13}$, and when R$_3$ is different from an alkoxy radical, then R$_1$ and R$_2$ do not simultaneously denote a hydrogen atom;

(B) compounds of formula (II) below:

$$\text{B—N}\!=\!\!=\!\!\text{N}-\!\!\!\underset{R_9}{\overset{R_8}{\bigcirc}}\!\!\!-\text{N}\underset{R_7}{\overset{R_6}{\diagup}} \quad X^- \qquad (II)$$

in which:
R$_6$ is chosen from a hydrogen atom and C$_1$–C$_4$ alkyl radicals;
R$_7$ is chosen from a hydrogen atom; alkyl radicals which may be unsubstituted or substituted with a —CN radical or an amino group; and a 4'-aminophenyl radical; or forms, with R$_6$, a heterocycle which optionally contains at least one oxygen heteroatom or nitrogen heteroatom and wherein said heterocycle is unsubstituted or substituted with at least one radical chosen from C$_1$–C$_4$ alkyl radicals;
R$_8$ and R$_9$, which may be identical or different, are chosen from a hydrogen atom, a chlorine atom, a bromine atom, an iodine atom, a fluorine atom, C$_1$–C$_4$ alkyl radicals, C$_1$–C$_4$ alkoxy radicals, and a —CN radical;
X$^-$ is an anion;

B is chosen from structures B1 to B6 below:

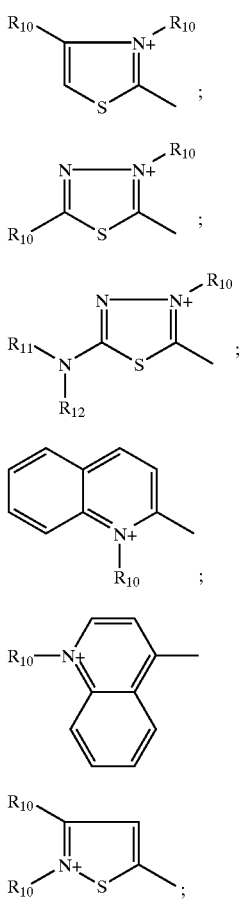

in which:

$R_{10}$ is chosen from $C_1$–$C_4$ alkyl radicals;

$R_{11}$ and $R_{12}$, which may be identical or different, are chosen from a hydrogen atom and $C_1$–$C_4$ alkyl radicals;

(C) compounds of formulae (III) or (III') below:

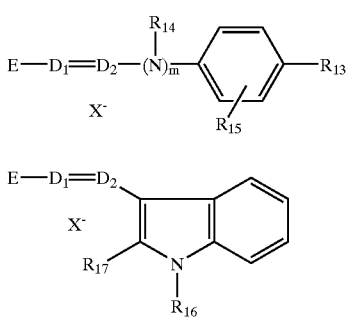

in which:

$R_{13}$ is chosen from a hydrogen atom, $C_1$–$C_4$ alkoxy radicals, a chlorine atom, a bromine atom, an iodine atom, a fluorine atom, and an amino radical;

$R_{14}$ is chosen from a hydrogen atom and $C_1$–$C_4$ alkyl radicals; or forms, with a carbon atom of the benzene ring, a heterocycle which optionally contains an oxygen heteroatom and wherein said heterocycle is unsubstituted or substituted with at least one $C_1$–$C_4$ alkyl group;

$R_{15}$ is chosen from a hydrogen atom, a chlorine atom, a bromine atom an iodine atom, and a fluorine atom;

$R_{16}$ and $R_{17}$, which may be identical or different, are chosen from a hydrogen atom and $C_1$–$C_4$ alkyl radicals;

$D_1$ and $D_2$, which may be identical or different, are chosen from a nitrogen atom and a —CH group;

m is an integer that equals 0 or 1;

$X^-$ is an anion;

wherein, when $R_{13}$ is an unsubstituted amino group, then $D_1$ and $D_2$ simultaneously are a —CH group, and m is 0; and E is chosen from structures E1 to E8 below:

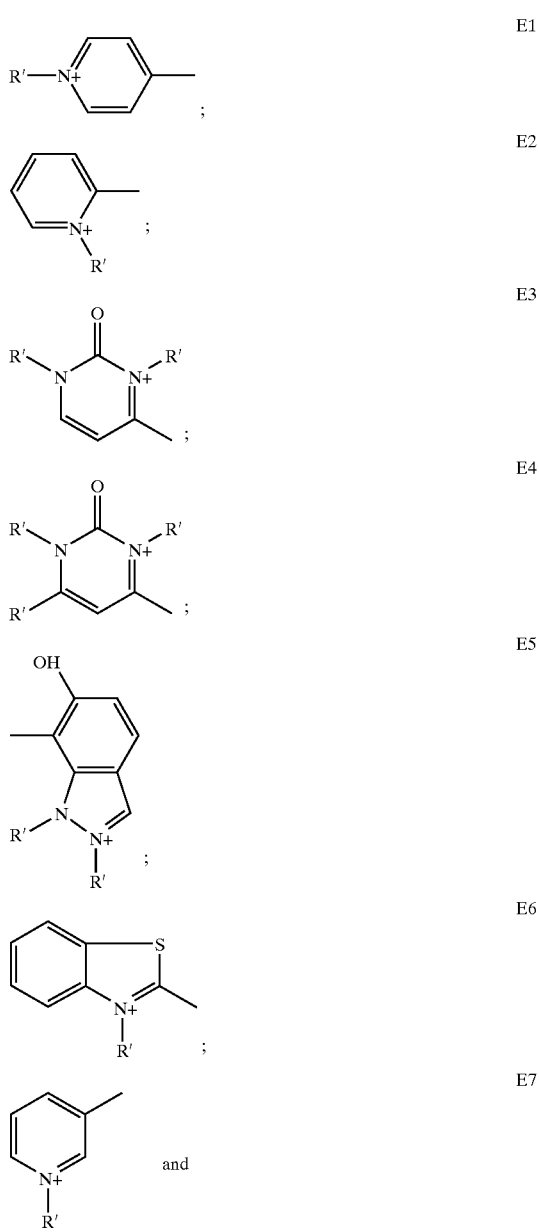

-continued

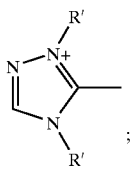
E8 in which
R' is chosen from $C_1$–$C_4$ alkyl radicals;
wherein, when m equals 0, and when $D_1$ is a nitrogen atom, then E may also be chosen from structure E9:

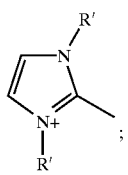
E9 in which:
R' is chosen from $C_1$–$C_4$ alkyl radicals; and (D) compounds of formula (IV) below:

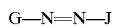
G—N=N—J    (IV)

in which:
G is a group chosen from structures $G_1$ to $G_3$:
in which:

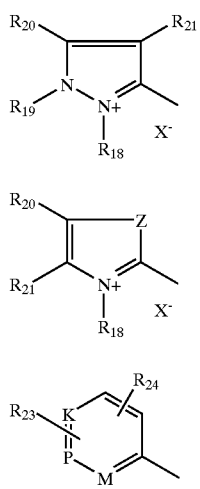

$R_{18}$ is chosen from $C_1$–$C_4$ alkyl radicals and a phenyl radical which is unsubstituted or substituted with at least one radical chosen from $C_1$–$C_4$ alkyl radicals, a fluorine atom, a bromine atom, a chlorine atom, and an iodine atom;

$R_{19}$ is chosen from $C_1$–$C_4$ alkyl radicals and a phenyl radical;

$R_{20}$ and $R_{21}$, which may be identical or different, are chosen from $C_1$–$C_4$ alkyl radicals and a phenyl radical; or form, together in $G_1$, a benzene ring which is substituted with at least one radical chosen from $C_1$–$C_4$ alkyl radicals, $C_1$–$C_4$ alkoxy radicals, and a $NO_2$ radical; or form, together in $G_2$, a benzene ring which is unsubstituted or substituted with at least one radical chosen from $C_1$–$C_4$ alkyl radicals, $C_1$–$C_4$ alkoxy radicals, and $NO_2$ radicals; and $R_{20}$ may also be chosen from a hydrogen atom;

Z is chosen from an oxygen atom, a sulphur atom, and —$NR_{19}$ radicals;

M, K, and P, each independently of the other, are chosen from —CH, —C($C_1$–$C_4$alkyl), and —$NR_{22}(X^-)_r$; r is 0 or 1;

$R_{22}$ is chosen from an $O^-$ atom, $C_1$–$C_4$ alkoxy radicals, and $C_1$–$C_4$ alkyl radicals;

$R_{23}$ and $R_{24}$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and an —$NO_2$ radical;

$X^-$ is an anion;
wherein J is chosen from:
(a) structures of $J_1$ below:

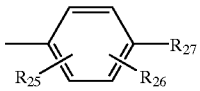
$J_1$ in which:
$R_{25}$ is chosen from a hydrogen atom, a chlorine atom, a bromine atom, an iodine atom, a fluorine atom, $C_1$–$C_4$ alkyl radicals, $C_1$–$C_4$ alkoxy radicals, an —OH radical, a —$NO_2$ radical, —$NHR_{28}$ radicals, —$NR_{29}R_{30}$ radicals, and —NHCO($C_1$–$C_4$alkyl) radicals; or forms, with $R_{26}$, a 5- or 6-member ring which optionally contains at least one heteroatom chosen from an oxygen atom, a nitrogen atom, and a sulfur atom;

$R_{26}$ is chosen from a hydrogen atom, a chlorine atom, a bromine atom, an iodine atom, a fluorine atom, $C_1$–$C_4$ alkyl radicals, and $C_1$–$C_4$ alkoxy radicals; or forms, with $R_{27}$ or $R_{28}$, a 5- or 6-member ring which optionally contains at least one heteroatom chosen from an oxygen atom, a nitrogen atom, and a sulfur atom;

$R_{27}$ is chosen from a hydrogen atom, an —OH radical, —$NHR_{28}$ radicals, and —$NR_{29}R_{30}$ radicals;

$R_{28}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, and a phenyl radical; and $R_{29}$ and $R_{30}$, which may be identical or different, are chosen from $C_1$–$C_4$ alkyl radicals, $C_1$–$C_4$ monohydroxyalkyl radicals, and $C_2$–$C_4$ polyhydroxyalkyl radicals; and (b) wherein J is further chosen from 5- and 6-member nitrogen-containing heterocycle groups which optionally contain at least one heteroatom and/or at least one carbonyl-containing group and wherein said heterocycle may be substituted or unsubstituted with at least one substituent chosen from $C_1$–$C_4$ alkyl radicals, an amino radical, and a phenyl radical.

41. A method according to claim 7, wherein said keratinous fibers are chosen from human keratinous fibers.

42. A method according to claim 7, wherein said human keratinous fibers are hairs.

43. A method for dyeing keratinous fibers, comprising:
separately storing a first composition and a second composition;

mixing said first composition with said second composition before applying the resultant mixture to said keratinous fibers; and applying said mixture to said keratinous fibers;

wherein said first composition comprises, in a medium suitable for dyeing, at least one cationic direct dye;

wherein said second composition comprises, in a medium suitable for dyeing, at least one oxidizing agent;

wherein either said first composition or said second composition comprises at least one anionic surfactant chosen from:
- (ii)$_1$—polyoxyethylenated ether carboxylic acids and salts thereof;
- (ii)$_2$—fatty glucamide sulphates;
- (ii)$_3$—alkyl galactoside uronates; and
- (ii)$_4$—anionic derivatives of alkyl polyglucosides;

wherein said at least one cationic direct dye is chosen from:

(A) compounds of formula (I) below:

$$A-D=D-\phantom{x}\text{(aryl)}-N(R_1)(R_2)$$ (I)

in which:

D is chosen from a nitrogen atom and a —CH group;

$R_1$ and $R_2$, which may be identical or different, are chosen from a hydrogen atom; $C_1$–$C_4$ alkyl radicals which may be unsubstituted or substituted with at least one radical chosen from a —CN radical, an —OH radical, and an —NH$_2$ radical; and a 4′-aminophenyl radical; or form, with each other or with a carbon atom of the benzene ring of formula (I), a heterocycle, which optionally contains an oxygen heteroatom or a nitrogen heteroatom and wherein said heterocycle may be unsubstituted or substituted with at least one radical chosen from $C_1$–$C_4$ radicals;

$R_3$ and $R'_3$, which may be identical or different, are chosen from a hydrogen atom, a chlorine atom, a bromine atom, an iodine atom, a fluorine atom, a cyano group, $C_1$–$C_4$ alkyl radicals, $C_1$–$C_4$ alkoxy radicals, and acetyloxy radicals;

X$^-$ is an anion;

A is chosen from structures $A_1$ to $A_{19}$ below:

-continued

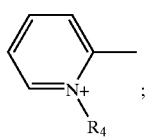
A13

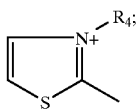
A14

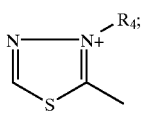
A15

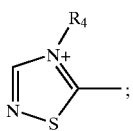
A16

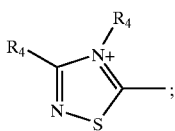
A17

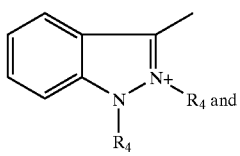
A18

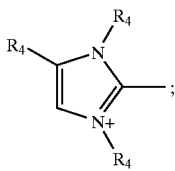
A19 in which:

$R_4$ is chosen from $C_1$–$C_4$ alkyl radicals which are unsubstituted or substituted with a hydroxyl radical; and $R_5$ is chosen from $C_1$–$C_4$ alkoxy radicals;

with the proviso that when D is —CH, when A is $A_4$ or $A_{13}$, and when $R_3$ is different from an alkoxy radical, then $R_1$ and $R_2$ do not simultaneously denote a hydrogen atom;

(B) compounds of formula (II) below:

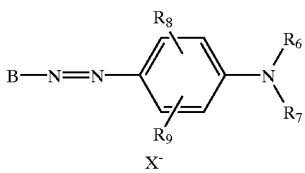
(II)

in which:

$R_6$ is chosen from a hydrogen atom and $C_1$–$C_4$ alkyl radicals;

$R_7$ is chosen from a hydrogen atom; alkyl radicals which may be unsubstituted or substituted with a —CN radical or an amino group; and a 4'-aminophenyl radical; or forms, with $R_6$, a heterocycle which optionally contains at least one oxygen heteroatom or nitrogen heteroatom and wherein said heterocycle is unsubstituted or substituted with at least one radical chosen from $C_1$–$C_4$ alkyl radicals;

$R_8$ and $R_9$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and a —CN radical;

$X^-$ is an anion;

B is chosen from structures B1 to B6 below:

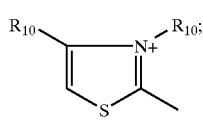
B1

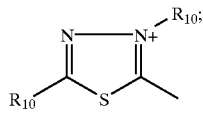
B2

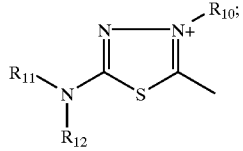
B3

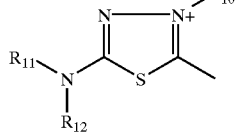
B4

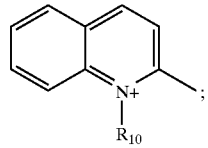
B5

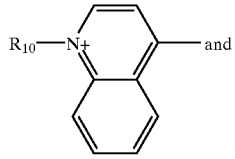
B6 in which:

$R_{10}$ is chosen from $C_1$–$C_4$ alkyl radicals;

$R_{11}$ and $R_{12}$, which may be identical or different, are chosen from a hydrogen atom and $C_1$–$C_4$ alkyl radicals;

(C) compounds of formulae (III) or (III') below:

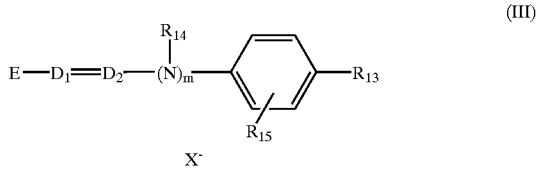
(III)

-continued (III')

[Structure III': indole with E—D₁=D₂— at 3-position, R₁₇ at 2-position, R₁₆ on N, X⁻]

in which:

R₁₃ is chosen from a hydrogen atom, C₁–C₄ alkoxy radicals, a chlorine atom, a bromine atom, an iodine atom, a fluorine atom, and an amino radical;

R₁₄ is chosen from a hydrogen atom and C₁–C₄ alkyl radicals; or forms, with a carbon atom of the benzene ring, a heterocycle which optionally contains an oxygen heteroatom and wherein said heterocycle is unsubstituted or substituted with at least one C₁–C₄ alkyl group;

R₁₅ is chosen from a hydrogen atom, a chlorine atom, a bromine atom, an iodine atom, and a fluorine atom;

R₁₆ and R₁₇, which may be identical or different, are chosen from a hydrogen atom and C₁–C₄ alkyl radicals;

D₁ and D₂, which may be identical or different, are chosen from a nitrogen atom and a —CH group;

m is an integer that equals 0 or 1;

X⁻ is an anion;

wherein, when R₁₃ is an unsubstituted amino group, then D₁ and D₂ simultaneously are a —CH group, and m is 0; and E is chosen from structures E1 to E8 below:

E1: R'—N⁺(pyridinium, 4-position attachment);

E2: pyridinium attached at 2-position, N-R';

E3: pyrimidinone with R' on each N, N⁺, methyl substituent;

E4: pyrimidinone with R' on each N, N⁺, two methyl substituents;

E5: hydroxy-methyl indazolium with R' on both N's;

E6: benzothiazolium with methyl, N-R';

E7: 3-methyl pyridinium, N-R'; and

E8: triazolium with R' substituents;

in which
R' is chosen from C₁–C₄ alkyl radicals;
wherein, when m equals 0, and when D₁ is a nitrogen atom, then E may also be chosen from structure E9:

E9: imidazolium with R' on both N's, methyl at 2-position;

in which:
R' is chosen from C₁–C₄ alkyl radicals; and (D) compounds of formula (IV) below:

G—N=N—J   (IV)

in which:
G is a group chosen from structures G₁ to G₃:

G₁: pyrazolium with R₂₀, R₂₁, R₁₉ (on N), R₁₈ (on N⁺), methyl; X⁻

-continued

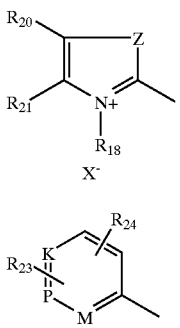

G2

G3 in which:

R$_{18}$ is chosen from C$_1$–C$_4$ alkyl radicals and a phenyl radical which is unsubstituted or substituted with at least one radical chosen from C$_1$–C$_4$ alkyl radicals, a fluorine atom, a bromine atom, a chlorine atom, and an iodine atom;

R$_{19}$ is chosen from C$_1$–C$_4$ alkyl radicals and a phenyl radical;

R$_{20}$ and R$_{21}$, which may be identical or different, are chosen from C$_1$–C$_4$ alkyl radicals and a phenyl radical; or form, together in G$_1$, a benzene ring which is substituted with at least one radical chosen from C$_1$–C$_4$ alkyl radicals, C$_1$–C$_4$ alkoxy radicals, and a NO$_2$ radical; or form, together in G$_2$, a benzene ring which is unsubstituted or substituted with at least one radical chosen from C$_1$–C$_4$ alkyl radicals, C$_1$–C$_4$ alkoxy radicals, and NO$_2$ radicals; and R$_{20}$ may also be chosen from a hydrogen atom;

Z is chosen from an oxygen atom, a sulphur atom, and —NR$_{19}$ radicals;

M, K, and P, each independently of the other, are chosen from —CH, —C(C$_1$–C$_4$alkyl), and —NR$_{22}$(X$^-$)$_r$; r is 0 or 1;

R$_{22}$ is chosen from an O$^-$ atom, C$_1$–C$_4$ alkoxy radicals, and C$_1$–C$_4$ alkyl radicals;

R$_{23}$ and R$_{24}$, which may be identical or different, are chosen from a hydrogen atom, a chlorine atom, a bromine atom, an iodine atom, a fluorine atom, C$_1$–C$_4$ alkyl radicals, C$_1$–C$_4$ alkoxy radicals, and an —NO$_2$ radical;

X$^-$ is an anion;

wherein J is chosen from:

(a) structures of J$_1$ below:

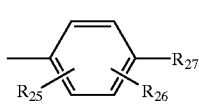

J$_1$ in which:

R$_{25}$ is chosen from a hydrogen atom, a chlorine atom, a bromine atom, an iodine atom, a fluorine atom, C$_1$–C$_4$ alkyl radicals, C$_1$–C$_4$ alkoxy radicals, an —OH radical, a —NO$_2$ radical, —NHR$_{28}$ radicals, —NR$_{29}$R$_{30}$ radicals, and —NHCO(C$_1$–C$_4$alkyl) radicals; or forms, with R$_{26}$, a 5- or 6-member ring which optionally contains at least one heteroatom chosen from an oxygen atom, a nitrogen atom, and a sulfur atom;

R$_{26}$ is chosen from a hydrogen atom, a chlorine atom, a bromine atom, an iodine atom, a fluorine atom, C$_1$–C$_4$ alkyl radicals, and C$_1$–C$_4$ alkoxy radicals; or forms, with R$_{27}$ or R$_{28}$, a 5- or 6-member ring which optionally contains at least one heteroatom chosen from an oxygen atom, a nitrogen atom, and a sulfur atom;

R$_{27}$ is chosen from a hydrogen atom, an —OH radical, —NHR28 radicals, and —NR$_{29}$R$_{30}$ radicals;

R$_{28}$ is chosen from a hydrogen atom, C$_1$–C$_4$ alkyl radicals, C$_1$–C$_4$ monohydroxyalkyl radicals, C$_2$–C$_4$ polyhydroxyalkyl radicals, and a phenyl radical; and R$_{29}$ and R$_{30}$, which may be identical or different, are chosen from C$_1$–C$_4$ alkyl radicals, C$_1$–C$_4$ monohydroxyalkyl radicals, and C$_2$–C$_4$ polyhydroxyalkyl radicals; and (b) wherein J is further chosen from 5- and 6-member nitrogen-containing heterocycle groups which optionally contain at least one heteroatom and/or at least one carbonyl-containing group and wherein said heterocycle may be substituted or unsubstituted with at least one substituent chosen from C$_1$–C$_4$ alkyl radicals, an amino radical, and a phenyl radical.

44. A method according to claim 43, wherein said keratinous fibers are chosen from human keratinous fibers.

45. A method according to claim 44, wherein said human keratinous fibers are hairs.

46. A multicompartment dyeing kit, comprising a first compartment containing a first composition and a second compartment containing a second composition;

wherein said first composition comprises, in a medium suitable for dyeing, at least one cationic direct dye and at least one oxidation base;

wherein said second composition comprises, in a medium suitable for dyeing, at least one oxidizing agent;

wherein either said first composition or said second composition comprises at least one anionic surfactant chosen from:

(ii)$_6$—polyoxyethylenated ether carboxylic acids and salts thereof;

(ii)$_7$—fatty glucamide sulphates;

(ii)$_8$—alkyl galactoside uronates; and (ii)$_9$—anionic derivatives of alkyl polyglucosides;

wherein said at least one cationic direct dye is chosen from:

(A) compounds of formula (I) below:

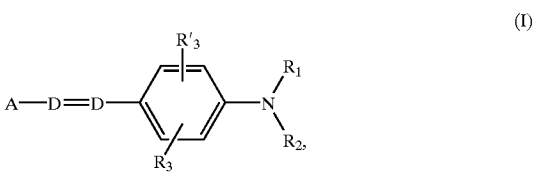

(I)

in which:

D is chosen from a nitrogen atom and a —CH group;

R$_1$ and R$_2$, which may be identical or different, are chosen from a hydrogen atom; C$_1$–C$_4$ alkyl radicals which may be unsubstituted or substituted with at least one radical chosen from a —CN radical, an —OH radical, and an —NH$_2$ radical; and a 4'-aminophenyl radical; or form, with each other or with a carbon atom of the benzene ring of formula (I), a heterocycle, which optionally contains an oxygen heteroatom or a nitrogen heteroatom and wherein said heterocycle may be unsubstituted or substituted with at least one radical chosen from C$_1$–C$_4$ radicals;

R₃ and R'₃, which may be identical or different, are chosen from a hydrogen atom, a chlorine atom, a bromine atom, an iodine atom, a fluorine atom, a cyano group, C₁–C₄ alkyl radicals, C₁–C₄ alkoxy radicals, and acetyloxy radicals;

X⁻ is an anion;

A is chosen from structures A₁ to A₁₉ below:

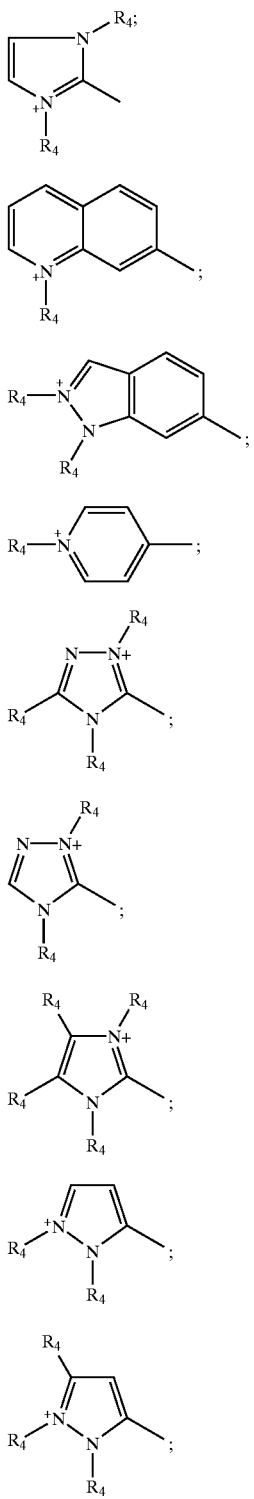

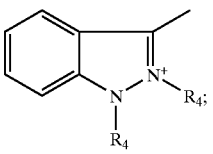

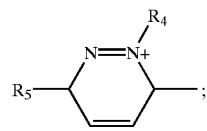

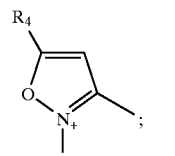

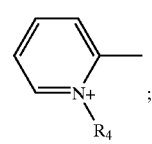

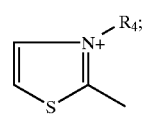

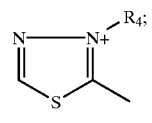

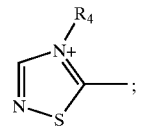

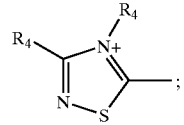

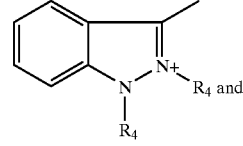

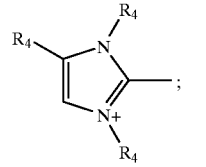

in which:

R₄ is chosen from C₁–C₄ alkyl radicals which are unsubstituted or substituted with a hydroxyl radical; and R₅ is chosen from C₁–C₄ alkoxy radicals;

with the proviso that when D is —CH, when A is $A_4$ or $A_{13}$, and when $R_3$ is different from an alkoxy radical, then $R_1$ and $R_2$ do not simultaneously denote a hydrogen atom;

(B) compounds of formula (II) below:

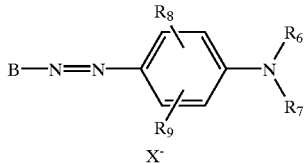

(II)

in which:

$R_6$ is chosen from a hydrogen atom and $C_1$–$C_4$ alkyl radicals;

$R_7$ is chosen from a hydrogen atom; alkyl radicals which may be unsubstituted or substituted with a —CN radical or an amino group; and a 4'-aminophenyl radical; or forms, with $R_6$, a heterocycle which optionally contains at least one oxygen heteroatom or nitrogen heteroatom and wherein said heterocycle is unsubstituted or substituted with at least one radical chosen from $C_1$–$C_4$ alkyl radicals;

$R_8$ and $R_9$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and a —CN radical;

$X^-$ is an anion;

B is chosen from structures B1 to B6 below:

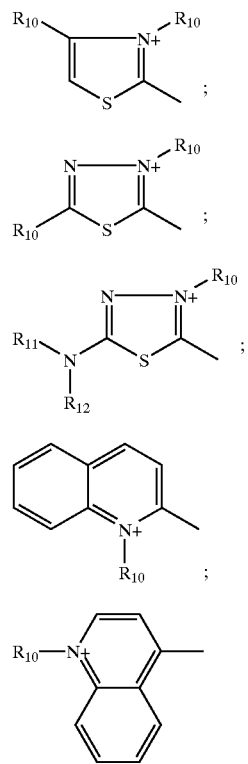

and

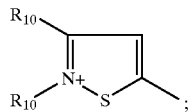

B6 in which:

$R_{10}$ is chosen from $C_1$–$C_4$ alkyl radicals;

$R_{11}$ and $R_{12}$, which may be identical or different, are chosen from a hydrogen atom and $C_1$–$C_4$ alkyl radicals;

(C) compounds of formulae (III) or (III') below:

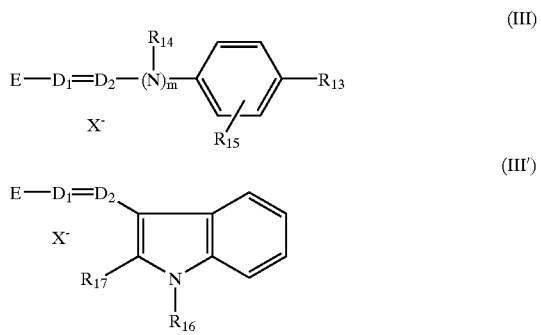

in which:

$R_{13}$ is chosen from a hydrogen atom, $C_1$–$C_4$ alkoxy radicals, a chlorine atom, a bromine atom, an iodine atom, a fluorine atom, and an amino radical;

$R_{14}$ is chosen from a hydrogen atom and $C_1$–$C_4$ alkyl radicals; or forms, with a carbon atom of the benzene ring, a heterocycle which optionally contains an oxygen heteroatom and wherein said heterocycle is unsubstituted or substituted with at least one $C_1$–$C_4$ alkyl group;

$R_{15}$ is chosen from a hydrogen atom, a chlorine atom, a bromine atom, an iodine atom, and a fluorine atom;

$R_{16}$ and $R_{17}$, which may be identical or different, are chosen from a hydrogen atom and $C_1$–$C_4$ alkyl radicals;

$D_1$ and $D_2$, which may be identical or different, are chosen from a nitrogen atom and a —CH group;

m is an integer that equals 0 or 1;

$X^-$ is an anion;

wherein, when $R_{13}$ is an unsubstituted amino group, then $D_1$ and $D_2$ simultaneously are a —CH group, and m is 0; and E is chosen from structures E1 to E8 below:

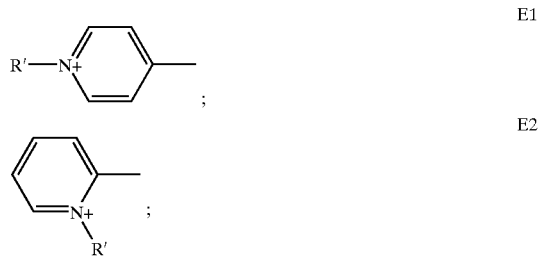

-continued

E3

[chemical structure: pyrimidinone with R' on both N, one N+, methyl substituent]

E4

[chemical structure: pyrimidinone with R' on both N and one R' on C, one N+, methyl]

E5

[chemical structure: indazole with OH, methyl, R' on N, R' on N+]

E6

[chemical structure: benzothiazole with methyl, R' on N+]

E7

[chemical structure: pyridine with methyl, R' on N+]

and

E8

[chemical structure: triazole with R' groups on N atoms, methyl]

in which
R' is chosen from $C_1$–$C_4$ alkyl radicals;
wherein, when m equals 0, and when $D_1$ is a nitrogen atom, then E may also be chosen from structure E9:

E9

[chemical structure: imidazole with R' on N atoms, methyl]

in which:
R' is chosen from $C_1$–$C_4$ alkyl radicals; and (D) compounds of formula (IV) below:

$$G-N=N-J \qquad (IV)$$

in which:
G is a group chosen from structures $G_1$ to $G_3$:

$G_1$

[chemical structure: pyrazolium with $R_{20}$, $R_{21}$, $R_{19}$, $R_{18}$, X−, methyl]

$G_2$

[chemical structure: five-membered ring with $R_{20}$, $R_{21}$, Z, $R_{18}$, X−, methyl]

$G_3$

[chemical structure: six-membered ring with $R_{23}$, K, $R_{24}$, P, M, methyl]

in which:
$R_{18}$ is chosen from $C_1$–$C_4$ alkyl radicals and a phenyl radical which is unsubstituted or substituted with at least one radical chosen from $C_1$–$C_4$ alkyl radicals, a fluorine atom, a bromine atom, a chlorine atom, and an iodine atom;
$R_{19}$ is chosen from $C_1$–$C_4$ alkyl radicals and a phenyl radical;
$R_{20}$ and $R_{21}$, which may be identical or different, are chosen from $C_1$–$C_4$ alkyl radicals and a phenyl radical; or form, together in $G_1$, a benzene ring which is substituted with at least one radical chosen from $C_1$–$C_4$ alkyl radicals, $C_1$–$C_4$ alkoxy radicals, and a $NO_2$ radical; or form, together in $G_2$, a benzene ring which is unsubstituted or substituted with at least one radical chosen from $C_1$–$C_4$ alkyl radicals, $C_1$–$C_4$ alkoxy radicals, and $NO_2$ radicals; and $R_{20}$ may also be chosen from a hydrogen atom;
Z is chosen from an oxygen atom, a sulphur atom, and —$NR_{19}$ radicals;
M, K, and P, each independently of the other, are chosen from —CH, —C($C_1$–$C_4$alkyl), and —$NR_{22}(X^-)_r$; r is 0 or 1;
$R_{22}$ is chosen from an $O^-$ atom, $C_1$–$C_4$ alkoxy radicals, and $C_1$–$C_4$ alkyl radicals;
$R_{23}$ and $R_{24}$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and an —$NO_2$ radical;
$X^-$ is an anion;
wherein J is chosen from:
(a) structures of $J_1$ below:

$J_1$

[chemical structure: benzene ring with $R_{25}$, $R_{26}$, $R_{27}$ substituents]

in which:
$R_{25}$ is chosen from a hydrogen atom, a chlorine atom, a bromine atom, an iodine atom, a fluorine atom, $C_1$–$C_4$ alkyl radicals, $C_1$–$C_4$ alkoxy radicals, an —OH radical, a —NO$_2$ radical, —NHR$_{28}$ radicals, —NR$_{29}$R$_{30}$ radicals, and —NHCO(C$_1$–C$_4$alkyl) radicals; or forms, with R$_{26}$, a 5- or 6-member ring which optionally contains at least one heteroatom chosen from an oxygen atom, a nitrogen atom, and a sulfur atom;

R$_{26}$ is chosen from a hydrogen atom, a chlorine atom, a bromine atom, an iodine atom, a fluorine atom, C$_1$–C$_4$ alkyl radicals, and C$_1$–C$_4$ alkoxy radicals; or forms, with R$_{27}$ or R$_{28}$, a 5- or 6-member ring which optionally contains at least one heteroatom chosen from an oxygen atom, a nitrogen atom, and a sulfur atom;

R$_{27}$ is chosen from a hydrogen atom, an —OH radical, —NHR$_{28}$ radicals, and —NR$_{29}$R$_{30}$ radicals;

R$_{28}$ is chosen from a hydrogen atom, C$_1$–C$_4$ alkyl radicals, C$_1$–C$_4$ monohydroxyalkyl radicals, C$_2$–C$_4$ polyhydroxyalkyl radicals, and a phenyl radical; and R$_{29}$ and R$_{30}$, which may be identical or different, are chosen from C$_1$–C$_4$ alkyl radicals, C$_1$–C$_4$ monohydroxyalkyl radicals, and C$_2$–C$_4$ polyhydroxyalkyl radicals; and (b) wherein J is further chosen from 5- and 6- member nitrogen-containing heterocycle groups which optionally contain at least one heteroatom and/or at least one carbonyl-containing group and wherein said heterocycle may be substituted or unsubstituted with at least one substituent chosen from C$_1$–C$_4$ alkyl radicals, an amino radical, and a phenyl radical.

47. A multicompartment dyeing kit, comprising a first compartment containing a first composition and a second compartment containing a second composition;

wherein said first composition comprises, in a medium suitable for dyeing, at least one cationic direct dye;

wherein said second composition comprises, in a medium suitable for dyeing, at least one oxidizing agent;

wherein either said first composition or said second composition comprises at least one anionic surfactant chosen from:

(ii)$_1$—polyoxyethylenated ether carboxylic acids and salts thereof;

(ii)$_2$—fatty glucamide sulphates;

(ii)$_3$—alkyl galactoside uronates; and (ii)$_4$—anionic derivatives of alkyl polyglucosides;

wherein said at least one cationic direct dye is chosen from:

(A) compounds of formula (I) below:

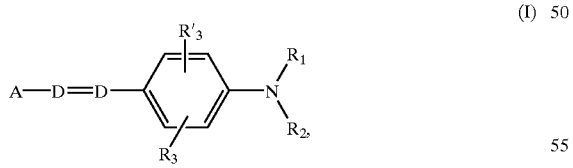

(I)

in which:

D is chosen from a nitrogen atom and a —CH group;

R$_1$ and R$_2$, which may be identical or different, are chosen from a hydrogen atom; C$_1$–C$_4$ alkyl radicals which may be unsubstituted or substituted with at least one radical chosen from a —CN radical, an —OH radical, and an —NH$_2$ radical; and a 4'-aminophenyl radical; or form, with each other or with a carbon atom of the benzene ring of formula (I), a heterocycle, which optionally contains an oxygen heteroatom or a nitrogen heteroatom and wherein said heterocycle may be unsubstituted or substituted with at least one radical chosen from C$_1$–C$_4$ radicals;

R$_3$ and R'$_3$, which may be identical or different, are chosen from a hydrogen atom, a chlorine atom, a bromine atom, an iodine atom, a fluorine atom, a cyano group, C$_1$–C$_4$ alkyl radicals, C$_1$–C$_4$ alkoxy radicals, and acetyloxy radicals;

X$^-$ is an anion;

A is chosen from structures A$_1$ to A$_{19}$ below:

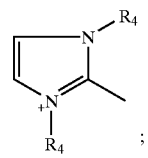

A$_1$

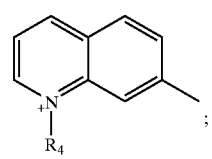

A$_2$

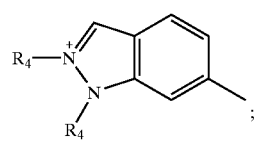

A$_3$

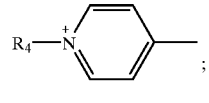

A$_4$

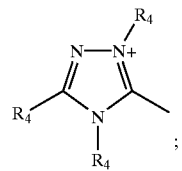

A$_5$

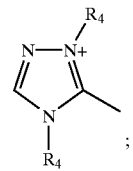

A$_6$

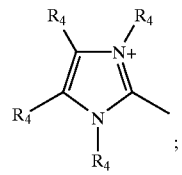

A$_7$

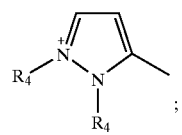

A$_8$

-continued

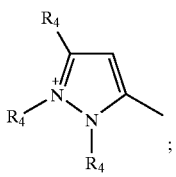  A_9

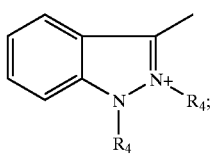  A_10

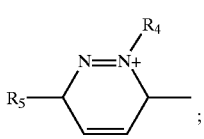  A_11

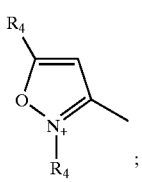  A_12

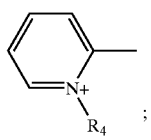  A_13

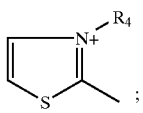  A_14

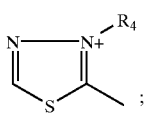  A_15

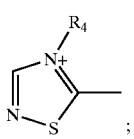  A_16

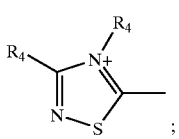  A_17

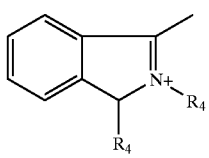 and  A_18

-continued

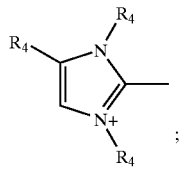  A_19 in which:
R_4 is chosen from $C_1-C_4$ alkyl radicals which are unsubstituted or substituted with a hydroxyl radical; and
R_5 is chosen from $C_1-C_4$ alkoxy radicals;
with the proviso that when D is —CH, when A is A_4 or A_13, and when R_3 is different from an alkoxy radical, then R_1 and R_2 do not simultaneously denote a hydrogen atom;

(B) compounds of formula (II) below:

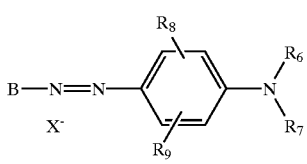

(II)

in which:
R_6 is chosen from a hydrogen atom and $C_1-C_4$ alkyl radicals;
R_7 is chosen from a hydrogen atom; alkyl radicals which may be unsubstituted or substituted with a —CN radical or an amino group; and a 4'-aminophenyl radical; or forms, with R_6, a heterocycle which optionally contains at least one oxygen heteroatom or nitrogen heteroatom and wherein said heterocycle is unsubstituted or substituted with at least one radical chosen from $C_1-C_4$ alkyl radicals;
R_8 and R_9 which may be identical or different, are chosen from a hydrogen atom, a chlorine atom, a bromine atom, an iodine atom, a fluorine atom, $C_1-C_4$ alkyl radicals, $C_1-C_4$ alkoxy radicals, and a —CN radical;
X⁻ is an anion;
B is chosen from structures B1 to B6 below:

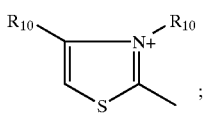  B1

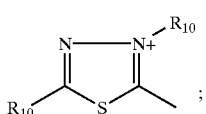  B2

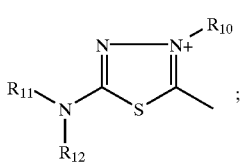  B3

-continued

B4

[structure: 2-methylquinolinium with N+–R10]

B5

[structure: 4-methylquinolinium with R10–N+]

and

B6

[structure: isothiazolium with R10 substituents, N+–S ring]

in which:
R₁₀ is chosen from $C_1$–$C_4$ alkyl radicals;
R₁₁ and R₁₂, which may be identical or different, are chosen from a hydrogen atom and $C_1$–$C_4$ alkyl radicals;

(C) compounds of formulae (III) or (III') below:

(III)

$$E—D_1{=}D_2—(N)_{\overline{m}}—\text{[benzene ring with }R_{14}, R_{13}, R_{15}\text{]}$$
$$X^-$$

(III')

$$E—D_1{=}D_2—\text{[indole ring with }R_{17}, R_{16}\text{]}$$
$$X^-$$

in which:
R₁₃ is chosen from a hydrogen atom, $C_1$–$C_4$ alkoxy radicals, a chlorine atom, a bromine atom, an iodine atom, a fluorine atom, and an amino radical;
R₁₄ is chosen from a hydrogen atom and $C_1$–$C_4$ alkyl radicals; or forms, with a carbon atom of the benzene ring, a heterocycle which optionally contains an oxygen heteroatom and wherein said heterocycle is unsubstituted or substituted with at least one $C_1$–$C_4$ alkyl group;
R₁₅ is chosen from a hydrogen atom, a chlorine atom, a bromine atom, an iodine atom, and a fluorine atom;
R₁₆ and R₁₇, which may be identical or different, are chosen from a hydrogen atom and $C_1$–$C_4$ alkyl radicals;
D₁ and D₂, which may be identical or different, are chosen from a nitrogen atom and a —CH group;
m is an integer that equals 0 or 1;
X⁻ is an anion;
wherein, when R₁₃ is an unsubstituted amino group, then D₁ and D₂ simultaneously are a —CH group, and m is 0; and
E is chosen from structures E1 to E8 below:

E1

[structure: R'—N+ pyridinium with methyl]

E2

[structure: 2-methylpyridinium N+–R']

E3

[structure: pyrimidinone with R' groups, N+]

E4

[structure: pyrimidinone with R' groups, N+, additional methyl]

E5

[structure: hydroxy-methyl-indazolium with R' groups, N+]

E6

[structure: 2-methylbenzothiazolium with N+–R']

E7

[structure: 3-methylpyridinium N+–R']

and

E8

[structure: triazolium with R' groups, N+]

in which
R' is chosen from $C_1$–$C_4$ alkyl radicals;
wherein, when m equals 0, and when D₁ is a nitrogen atom, then E may also be chosen from structure E9:

E9

[structure: imidazolium with R' groups, N+, methyl]

in which:
R' is chosen from $C_1$–$C_4$ alkyl radicals; and (D) compounds of formula (IV) below:

G—N=N—J    (IV)

in which:
G is a group chosen from structures $G_1$ to $G_3$:

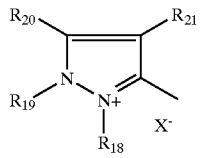

$G_1$

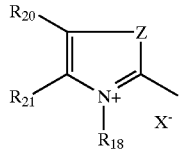

$G_2$

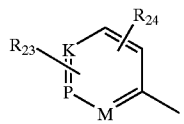

$G_3$ in which:
$R_{18}$ is chosen from $C_1$–$C_4$ alkyl radicals and a phenyl radical which is unsubstituted or substituted with at least one radical chosen from $C_1$–$C_4$ alkyl radicals, a fluorine atom, a bromine atom, a chlorine atom, and an iodine atom;
$R_{19}$ is chosen from $C_1$–$C_4$ alkyl radicals and a phenyl radical;
$R_{20}$ and $R_{21}$, which may be identical or different, are chosen from $C_1$–$C_4$ alkyl radicals and a phenyl radical; or form, together in $G_1$, a benzene ring which is substituted with at least one radical chosen from $C_1$–$C_4$ alkyl radicals, $C_1$–$C_4$ alkoxy radicals, and a $NO_2$ radical; or form, together in $G_2$, a benzene ring which is unsubstituted or substituted with at least one radical chosen from $C_1$–$C_4$ alkyl radicals, $C_1$–$C_4$ alkoxy radicals, and $NO_2$ radicals; and $R_{20}$ may also be chosen from a hydrogen atom;
Z is chosen from an oxygen atom, a sulphur atom, and —$NR_{19}$ radicals;
M, K, and P, each independently of the other, are chosen from —CH, —C($C_1$–$C_4$ alkyl), and —$NR_{22}(X^-)_r$; r is 0 or 1;
$R_{22}$ is chosen from an $O^-$ atom, $C_1$–$C_4$ alkoxy radicals, and $C_1$–$C_4$ alkyl radicals;
$R_{23}$ and $R_{24}$, which may be identical or different, are chosen from a hydrogen atom, a chlorine atom, a bromine atom, an iodine atom, a fluorine atom, $C_1$–$C_4$ alkyl radicals, $C_1$–$C_4$ alkoxy radicals, and an —$NO_2$ radical;
$X^-$ is an anion;
wherein J is chosen from:
(a) structures of $J_1$ below:

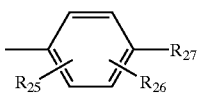

$J_1$ in which:
$R_{25}$ is chosen from a hydrogen atom, a chlorine atom, a bromine atom, an iodine atom, a fluorine atom, $C_1$–$C_4$ alkyl radicals, $C_1$–$C_4$ alkoxy radicals, an —OH radical, a —$NO_2$ radical, —$NHR_{28}$ radicals, —$NR_{29}R_{30}$ radicals, and —NHCO($C_1$–$C_4$alkyl) radicals; or forms, with $R_{26}$, a 5- or 6-member ring which optionally contains at least one heteroatom chosen from an oxygen atom, a nitrogen atom, and a sulfur atom;
$R_{26}$ is chosen from a hydrogen atom, a chlorine atom, a bromine atom, an iodine atom, a fluorine atom, $C_1$–$C_4$ alkyl radicals, and $C_1$–$C_4$ alkoxy radicals; or forms, with $R_{27}$ or $R_{28}$, a 5- or 6-member ring which optionally contains at least one heteroatom chosen from an oxygen atom, a nitrogen atom, and a sulfur atom;
$R_{27}$ is chosen from a hydrogen atom, an —OH radical, —$NHR_{28}$ radicals, and —$NR_{29}R_{30}$ radicals;
$R_{28}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, and a phenyl radical; and
$R_{29}$ and $R_{30}$, which may be identical or different, are chosen from $C_1$–$C_4$ alkyl radicals, $C_1$–$C_4$ monohydroxyalkyl radicals, and $C_2$–$C_4$ polyhydroxyalkyl radicals; and
(b) wherein J is further chosen from 5- and 6-member nitrogen-containing heterocycle groups which optionally contain at least one heteroatom and/or at least one carbonyl-containing group and wherein said heterocycle may be substituted or unsubstituted with at least one substituent chosen from $C_1$–$C_4$ alkyl radicals, an amino radical, and a phenyl radical.

* * * * *

UNITED STATES PATENT AND TRADEMARK OFFICE
CERTIFICATE OF CORRECTION

PATENT NO. : 6,530,959 B1
DATED : March 11, 2003
INVENTOR(S) : Gérard Lang et al.

It is certified that error appears in the above-identified patent and that said Letters Patent is hereby corrected as shown below:

Column 35,
Line 61, "4'-aminophneyl" should read -- 4'-aminophenyl --.
Lines 62-63, "formula (1)," should read -- formula (I), --.

Column 36,
In the structure $A_1$:

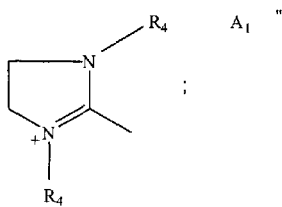

should read:

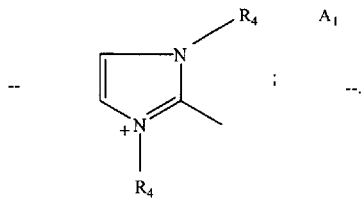

In the structure $A_3$:

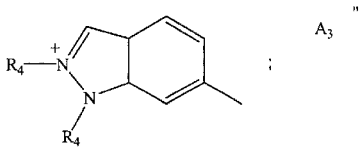

should read:

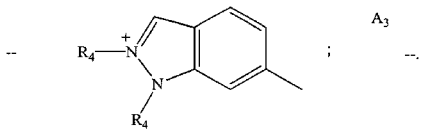

UNITED STATES PATENT AND TRADEMARK OFFICE
CERTIFICATE OF CORRECTION

PATENT NO. : 6,530,959 B1
DATED : March 11, 2003
INVENTOR(S) : Gérard Lang et al.

It is certified that error appears in the above-identified patent and that said Letters Patent is hereby corrected as shown below:

Column 39,
In the structure B3:

"
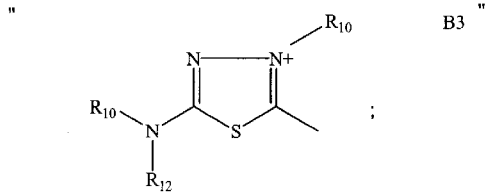
;"

should read:

--
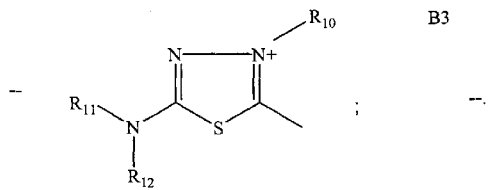
;--.

In the structure (III'):

"
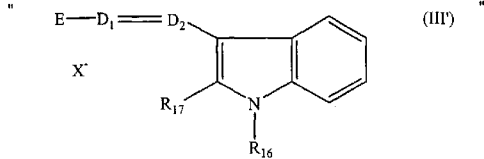
"

should read:

--
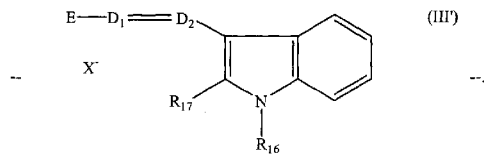
--.

UNITED STATES PATENT AND TRADEMARK OFFICE
CERTIFICATE OF CORRECTION

PATENT NO. : 6,530,959 B1
DATED : March 11, 2003
INVENTOR(S) : Gérard Lang et al.

It is certified that error appears in the above-identified patent and that said Letters Patent is hereby corrected as shown below:

Column 41,
In the structure $G_2$:

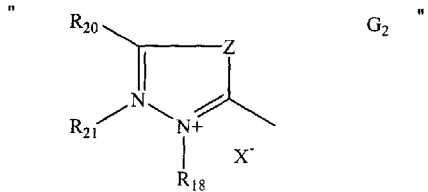

should read:

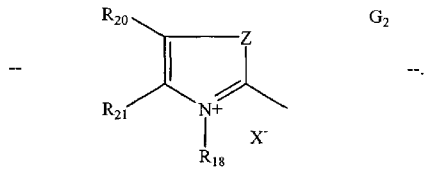

Column 42,
Line 52, "$C_2C_4$ polyhydroxyalkyl" should read -- $C_2$-$C_4$ polyhydroxyalkyl --.
Line 54, "6- member" should read -- 6-member --.

Column 43,
Line 29, after "$R_{31}$" delete the comma.

Column 49,
In the structure (I54), immediately to the right of "Cl⁻", change the semicolon to a period.
Line 55, after "formula (I) are", delete "chosen form".

Column 53,
In the structure $(IV)_3$:

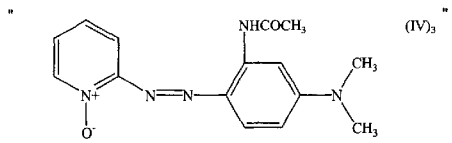

should read:

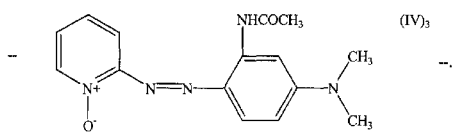

UNITED STATES PATENT AND TRADEMARK OFFICE
CERTIFICATE OF CORRECTION

PATENT NO. : 6,530,959 B1
DATED : March 11, 2003
INVENTOR(S) : Gérard Lang et al.

It is certified that error appears in the above-identified patent and that said Letters Patent is hereby corrected as shown below:

Column 56,
In the structure $(IV)_{27}$:

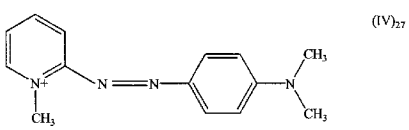

should read:

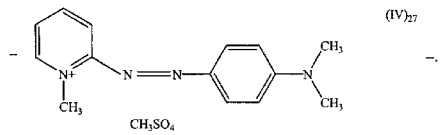

Column 61,
In the structure $(IV)_{67}$:

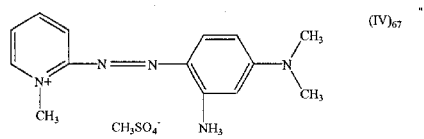

should read:

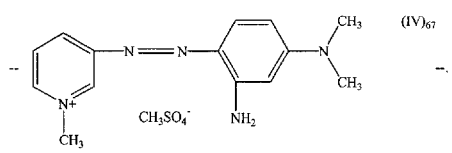

Column 63,
Line 22, "formula (VII)" should read -- formula (VIII) --.
Line 24, "$R^6(—OC_2H_4)_nOCH_2COOA$   (VII)" should read:

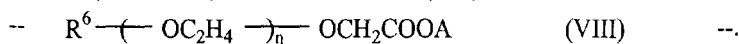

Column 65,
In the structure $A_3$:
should read:

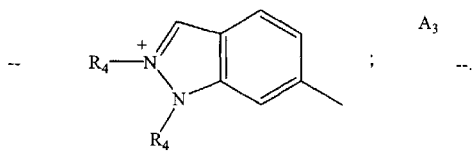

UNITED STATES PATENT AND TRADEMARK OFFICE
CERTIFICATE OF CORRECTION

PATENT NO. : 6,530,959 B1
DATED : March 11, 2003
INVENTOR(S) : Gérard Lang et al.

It is certified that error appears in the above-identified patent and that said Letters Patent is hereby corrected as shown below:

Column 70,
Line 44, "$C_1C_4$ alkyl" should read -- $C_1$-$C_4$ alkyl --.
Line 60, "-NHR28 radicals," should read -- -$NHR_{28}$ radicals, --.

Column 71,
Line 13, "$C_2$-$C_4$ olyhydroxyalkyl" should read -- $C_2$-$C_4$ polyhydroxyalkyl --.
Line 64, "$(ii)_1$ - alkyl" should read -- $(ii)_3$ - alkyl --.
Line 65, "$(ii)_2$ - anionic" should read -- $(ii)_4$ - anionic --.

Column 74,
In the structure $A_{18}$:

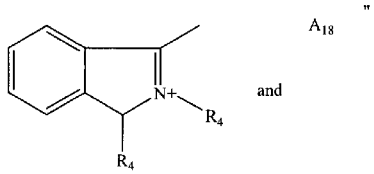 and should read:

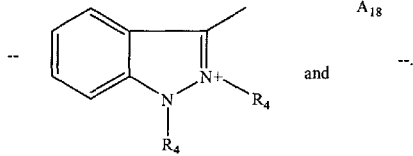 and --.

Column 76,
Line 5, after "a bromine atom an iodine atom, and a fluorine atom;" should read
-- a bromine atom, an iodine atom, and a fluorine atom; --.

Column 77,
Line 33, delete "in which:".
Before line 55, insert -- in which: --.

Column 78,
Line 61, "claim 7," should read -- claim 40, --.
Line 63, "claim 7," should read -- claim 41, --.

UNITED STATES PATENT AND TRADEMARK OFFICE
CERTIFICATE OF CORRECTION

PATENT NO. : 6,530,959 B1  Page 6 of 6
DATED : March 11, 2003
INVENTOR(S) : Gérard Lang et al.

It is certified that error appears in the above-identified patent and that said Letters Patent is hereby corrected as shown below:

Column 86,
Line 7, "-NHR28 radicals," should read -- -$NHR_{28}$ radicals, --.
Line 37, "$(ii)_6$ - polyoxyethylenated" should read -- $(ii)_1$ - polyoxyethylenated --.
Line 39, "$(ii)_7$ - fatty" should read -- $(ii)_2$ - fatty --.
Line 40, "$(ii)_8$ - alkyl" should read -- $(ii)_3$ - alkyl --.
Line 41, "$(ii)_9$ - anionic" should read -- $(ii)_4$ - anionic --.

Column 93,
Line 23, "6- member" should read -- 6-member --.

Column 95,
In the structure $A_{18}$:

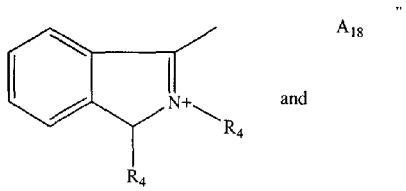

should read:

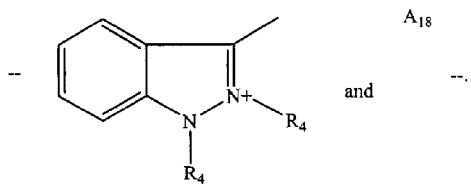

Signed and Sealed this

Seventeenth Day of June, 2003

JAMES E. ROGAN
*Director of the United States Patent and Trademark Office*